(12) United States Patent
Dutreix et al.

(10) Patent No.: US 7,595,302 B2
(45) Date of Patent: Sep. 29, 2009

(54) NUCLEIC ACIDS USEFUL FOR TRIGGERING TUMOR CELL LETHALITY

(75) Inventors: Marie Dutreix, L'Hay les Roses (FR); Jian-Sheng Sun, Saint Maur des Fosses (FR)

(73) Assignees: Institut Curie, Paris Cedex (FR); Centre National de la Recherche Scientifique (CNRS), Paris Cedex (FR); Museum National d'Histoire Naturelle, Paris Cedex (FR); Institut National de la Sante et de la Recherche Medicale (INSERM), Paris Cedex (FR)

( * ) Notice: Subject to any disclaimer, the term of this patent is extended or adjusted under 35 U.S.C. 154(b) by 172 days.

(21) Appl. No.: 10/576,818

(22) PCT Filed: Oct. 25, 2004

(86) PCT No.: PCT/EP2004/012857

§ 371 (c)(1),
(2), (4) Date: Jul. 19, 2006

(87) PCT Pub. No.: WO2005/040378

PCT Pub. Date: May 6, 2005

(65) Prior Publication Data

US 2007/0197458 A1    Aug. 23, 2007

(30) Foreign Application Priority Data

Oct. 24, 2003    (EP)    .................................. 03292666

(51) Int. Cl.
| | |
|---|---|
| *A61K 31/70* | (2006.01) |
| *C07H 21/04* | (2006.01) |
| *C07H 21/00* | (2006.01) |
| *C12Q 1/68* | (2006.01) |
| *C12P 19/34* | (2006.01) |

(52) U.S. Cl. ...................... 514/44; 536/23.1; 536/25.3; 435/6; 435/91.1

(58) Field of Classification Search ........................ None
See application file for complete search history.

(56) References Cited

U.S. PATENT DOCUMENTS

2003/0176376 A1 *   9/2003   Klem ........................... 514/44

FOREIGN PATENT DOCUMENTS

| EP | 0 978 561 A1 | 2/2000 |
|---|---|---|
| WO | WO 03/069306 A2 | 8/2003 |
| WO | WO 03/070914 A2 | 8/2003 |

OTHER PUBLICATIONS

Li et al. EMBO Journal 2001, vol. 20, pp. 3272-3281.*
Marthinet et al. Gene Therapy 2000, vol. 7, pp. 1224-1233.*
International Search Report of PCT/EP2004/012857, mailed Mar. 4, 2005.
Partial European Search Report of EP 03 29 2666, completed May 14, 2004.
Omori et al., "Suppression of a DNA double-strand break repair gene, *Ku70*, increases radio- and chemosensitivity in a human lung carcinoma cell line", DNA Repair, pp. 299-310, XP002279444.
Ohnishi et al., "In vitro and in vivo potentiation of radiosensitivity of malignant gliomas by antisense inhibition of the RAD51 gene", Biochemical and Biophysical Research Communications, vol. 245, No. 2, 1998, pp. 319-324, XP002279445.
Verrelle et al., "Modulation de la response cellulaire aux radiations ionisantes: vers de nouvelles cibles moleculaires?", Cancer/Radiother, vol. 1, 1997, pp. 484-493, XP002279446.

* cited by examiner

*Primary Examiner*—Tracy Vivlemore
(74) *Attorney, Agent, or Firm*—Nixon & Vanderhye P.C.

(57) ABSTRACT

The invention relates to double-stranded nucleic acid fragments comprising a chemically modified backbone and at least 4-1000 bp, preferably 8-500 bp, and most preferably 16-200 bp. The disclosed molecules (DRIL molecules) may interfere with DNA damage signaling and repair pathways, in particular the non homologous NHEJ pathway of double-stranded break repair. The invention discloses the application of the DRIL molecules as adjuvant compositions to be used in association with a DNA breaking treatment, particularly radiotherapy or chemotherapy, in combination with a pharmaceutically acceptable carrier, in an efficient amount to be introduced in the tumoral cell nuclei in order to trigger DNA repair induced lethality (DRIL in short) of tumoral cells/tissues.

22 Claims, 12 Drawing Sheets

Figure 4:
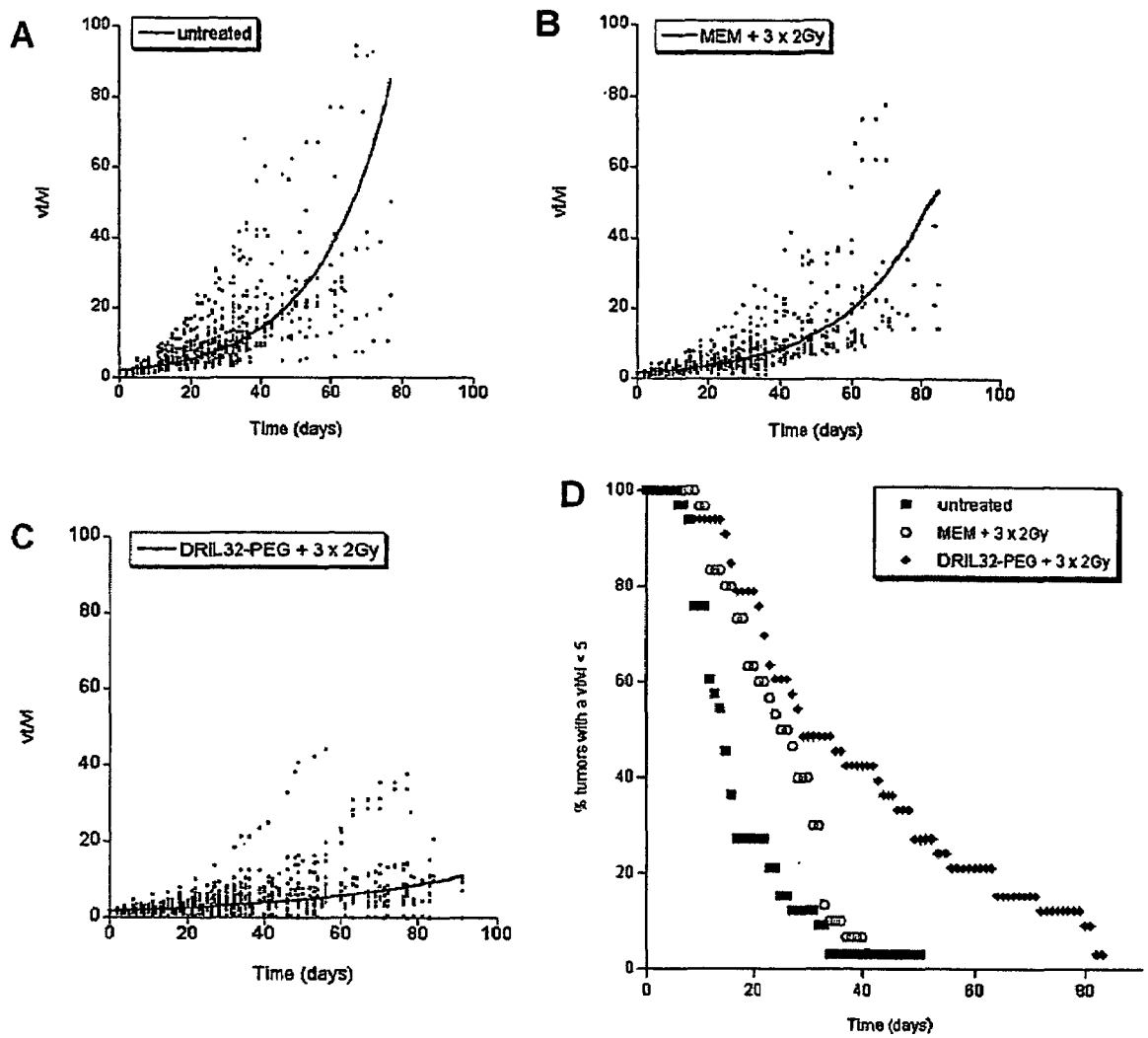

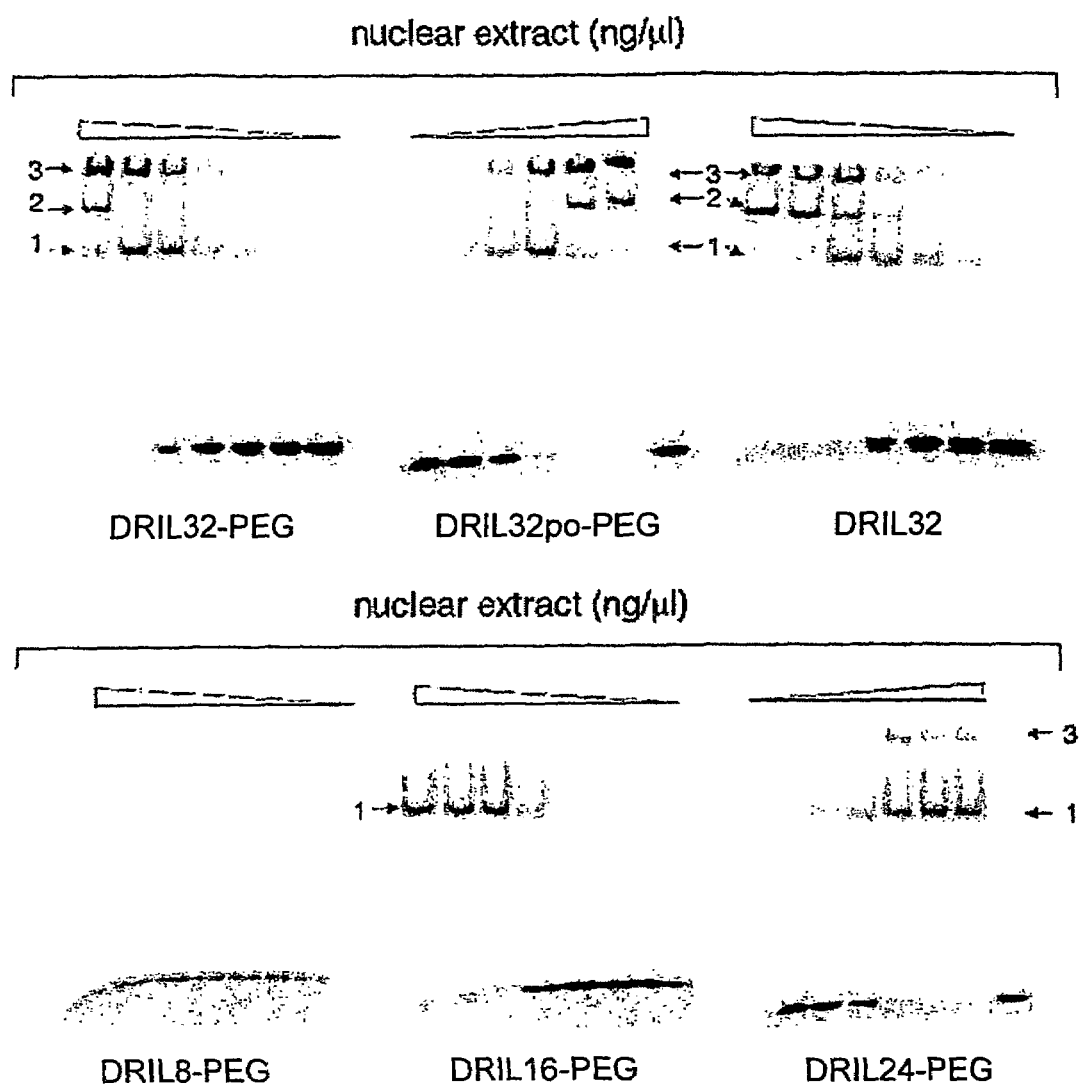
Figure 1.1

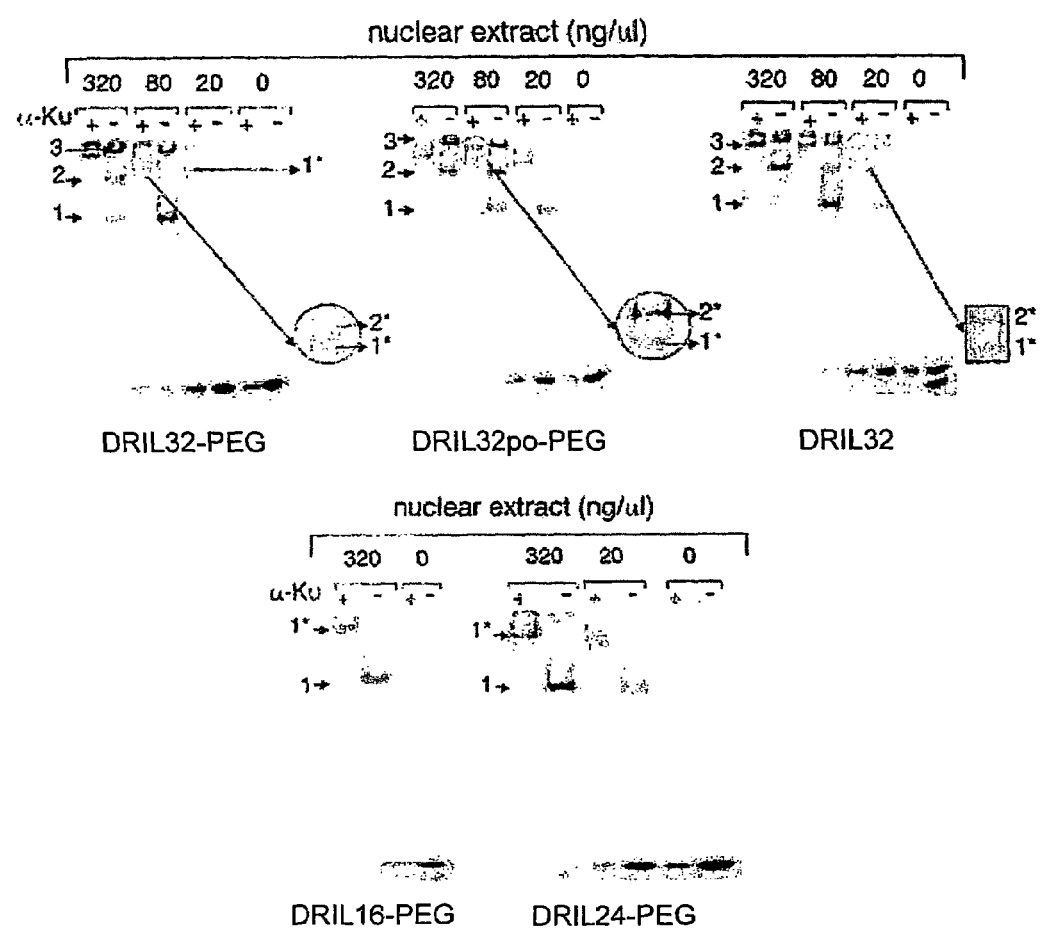
Figure 1.2

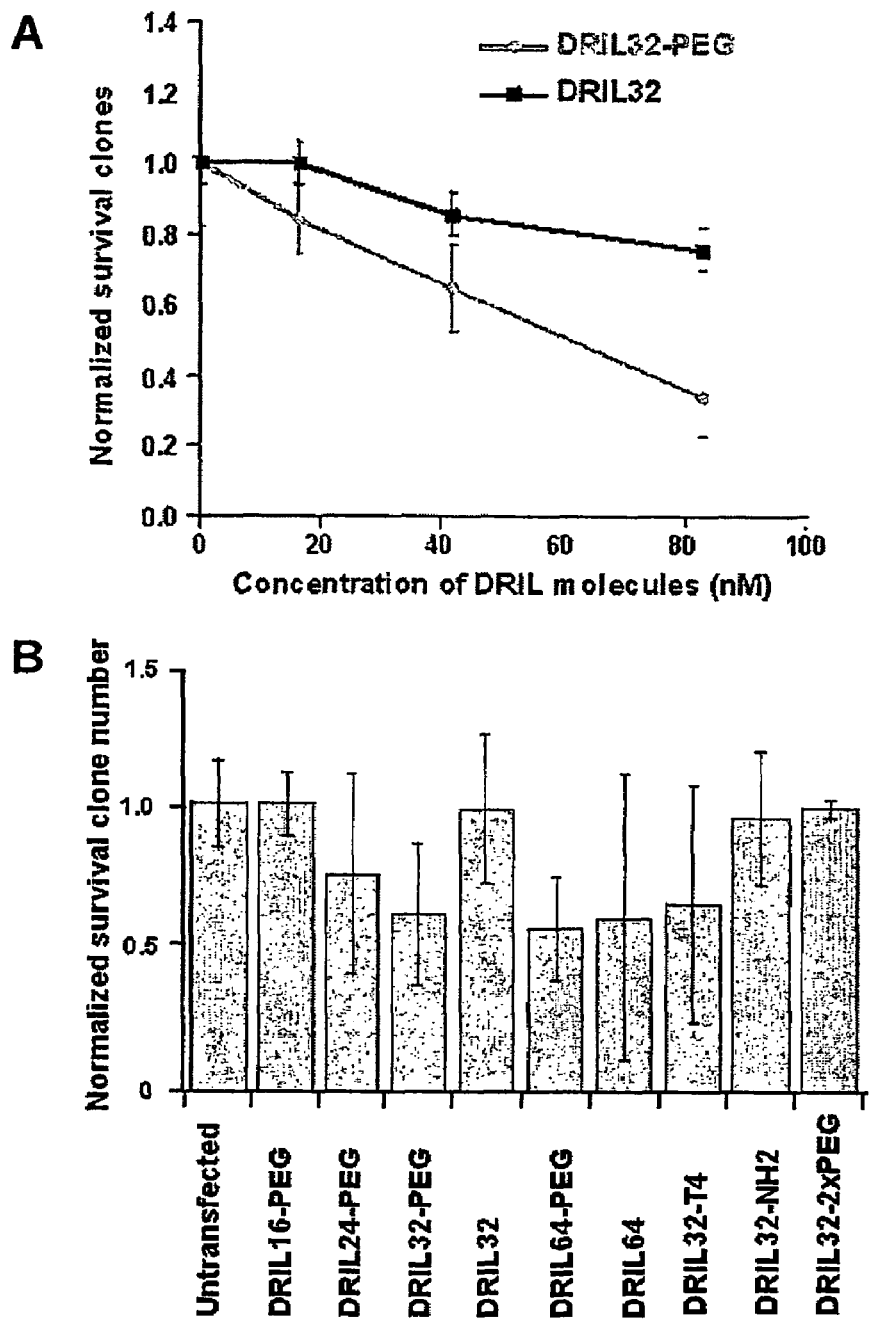
Figure 2.1

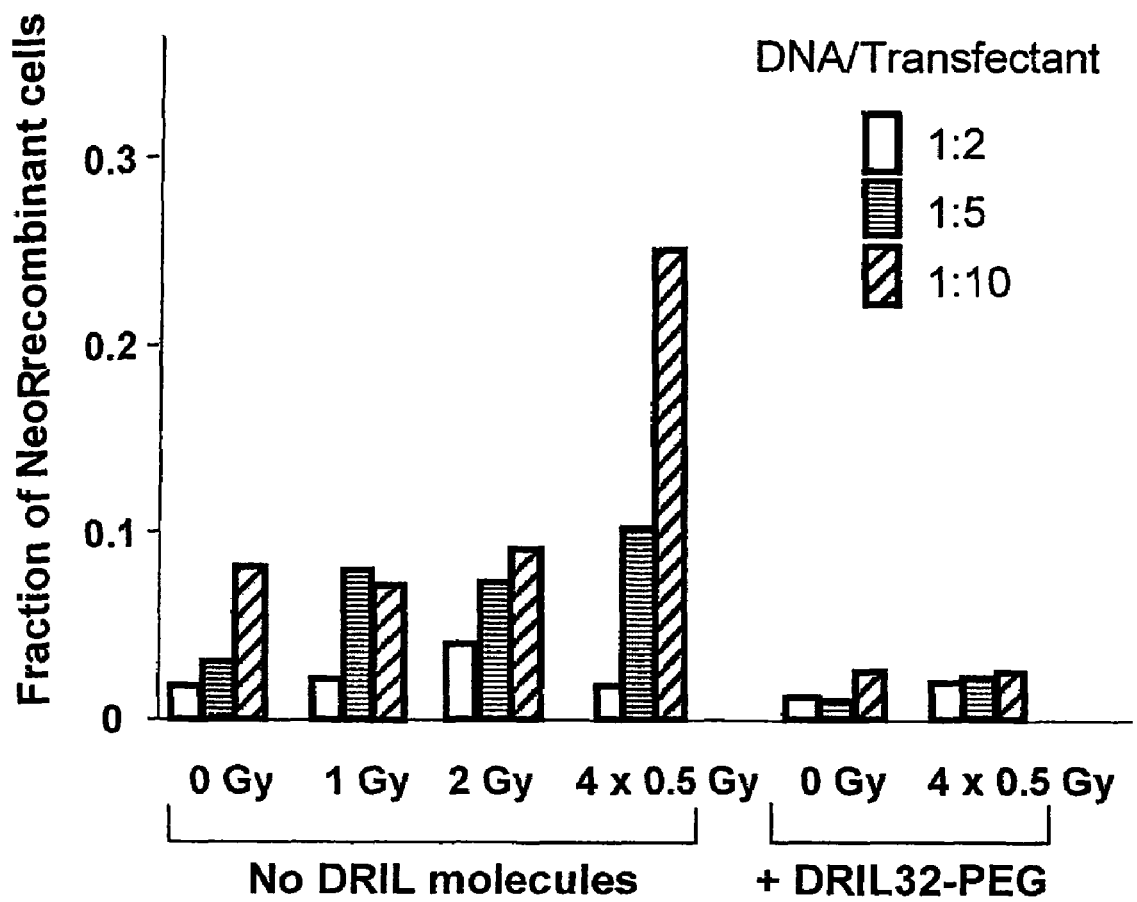
Figure 2.2

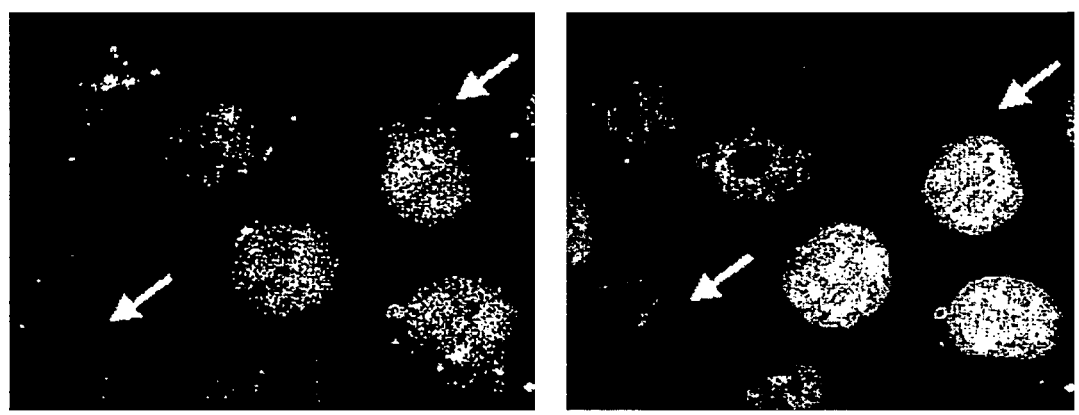
Figure 2.3

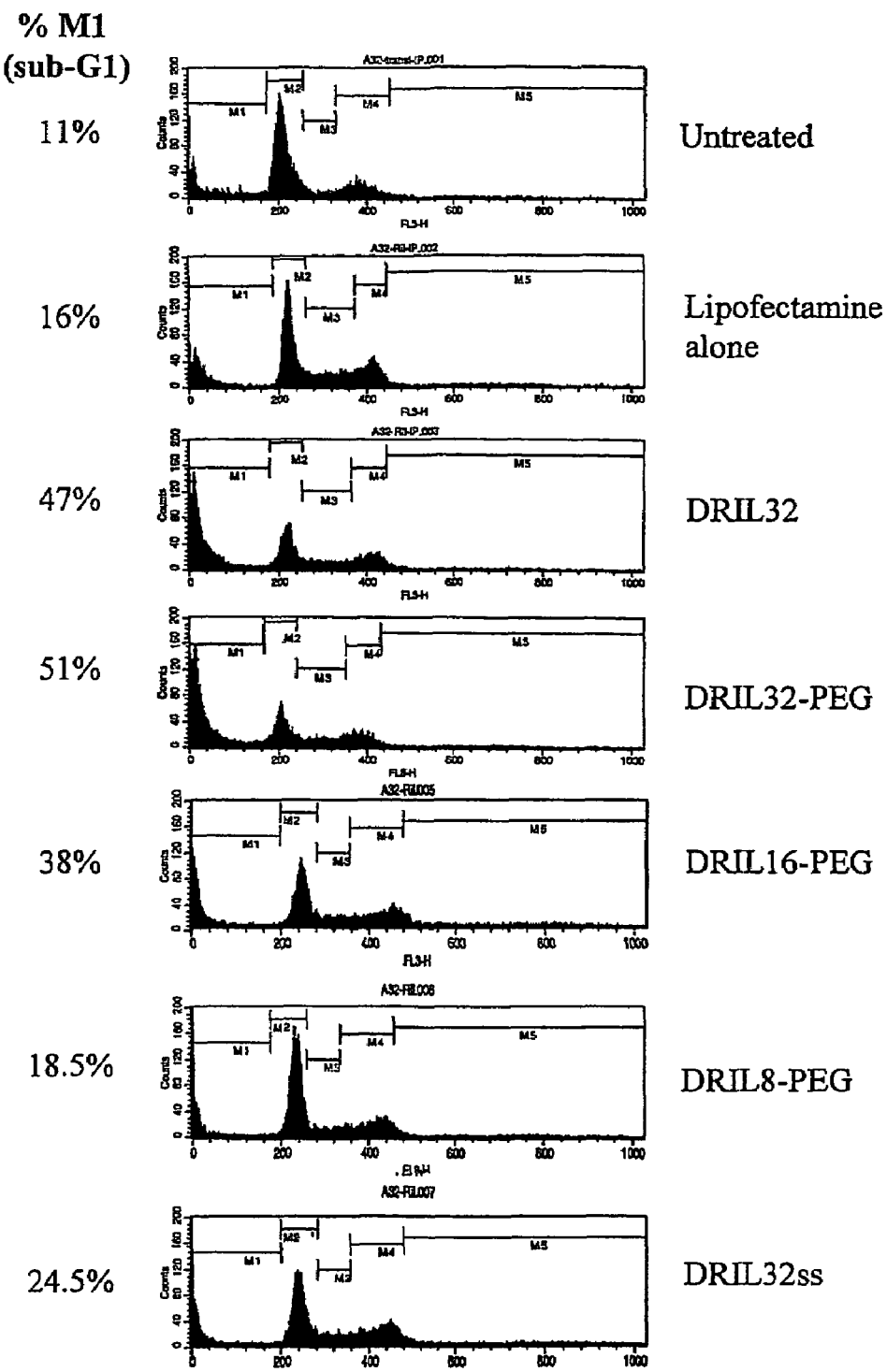
Figure 3.1.

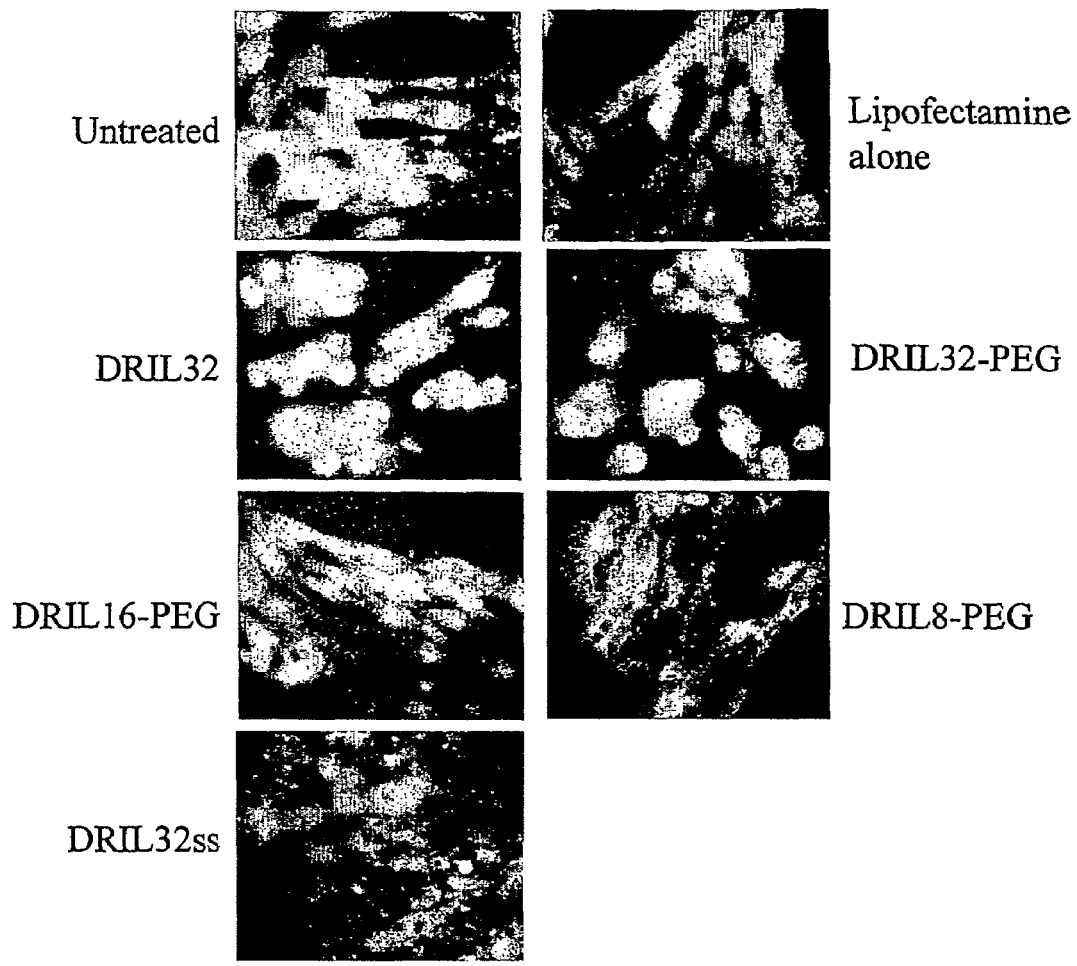
Figure 3.2

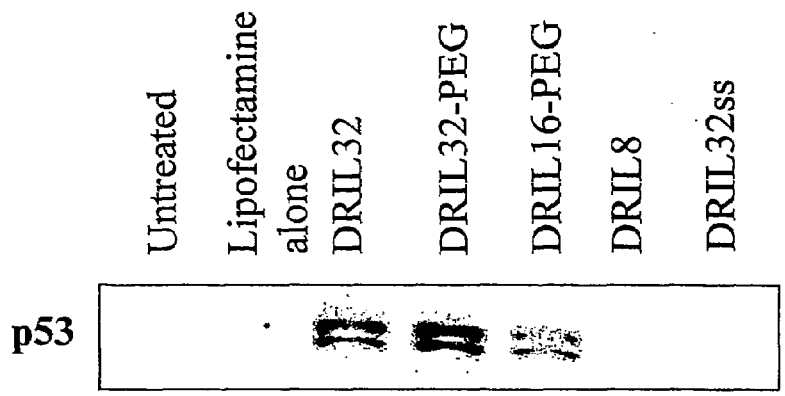
Figure 3.3
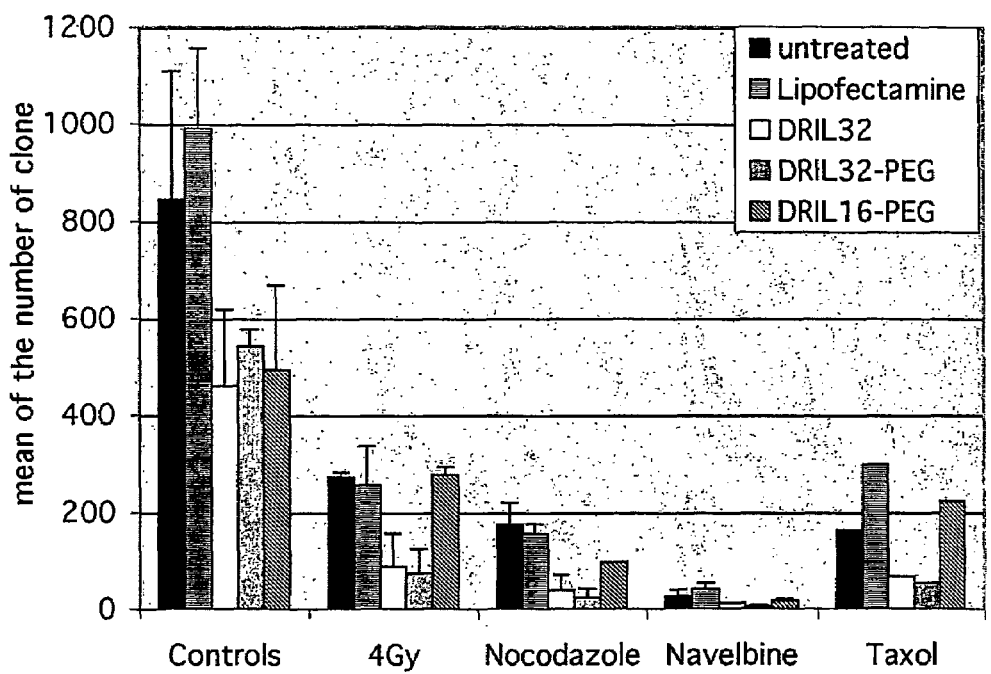
Figure 3.4

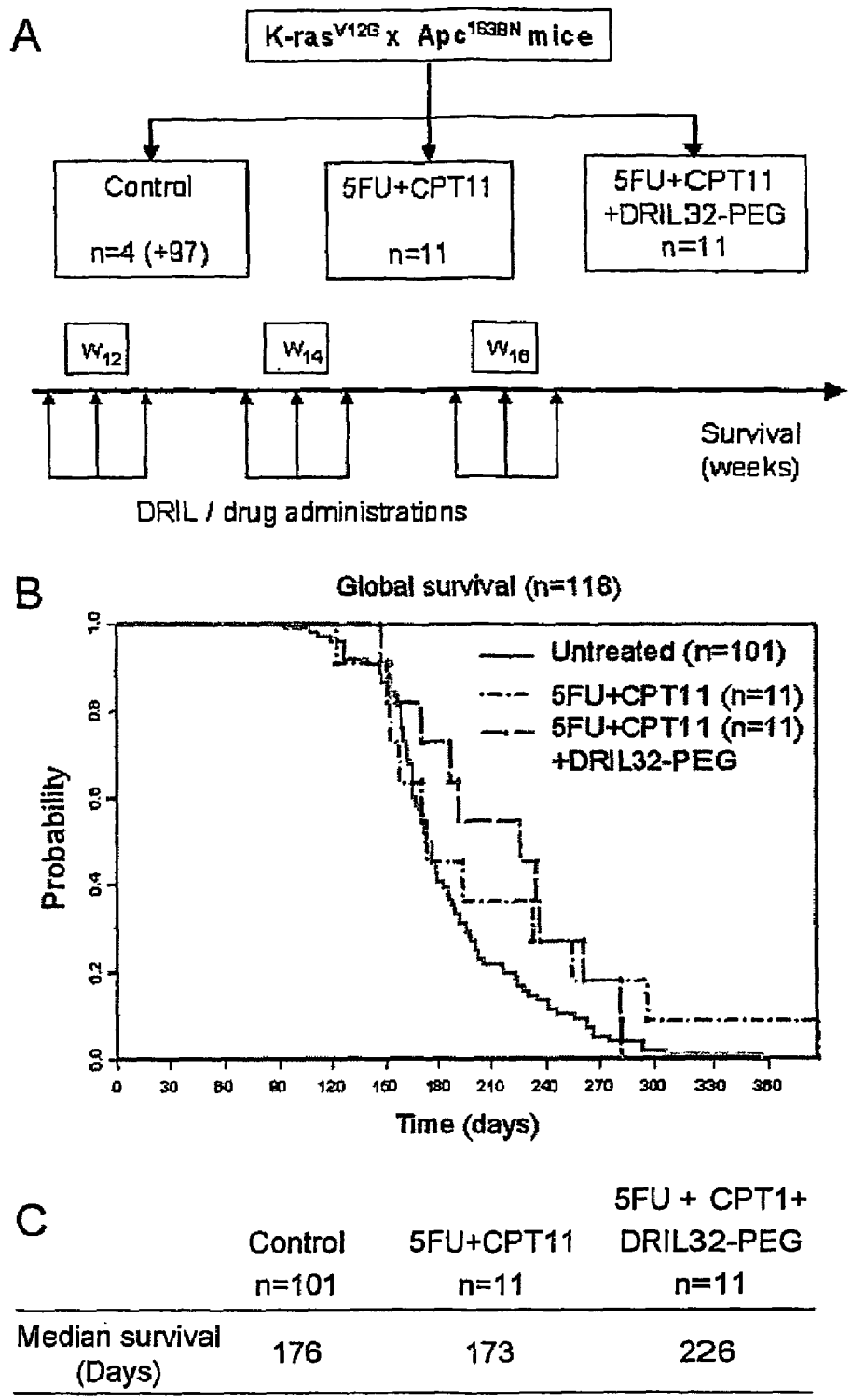
Figure 5.1

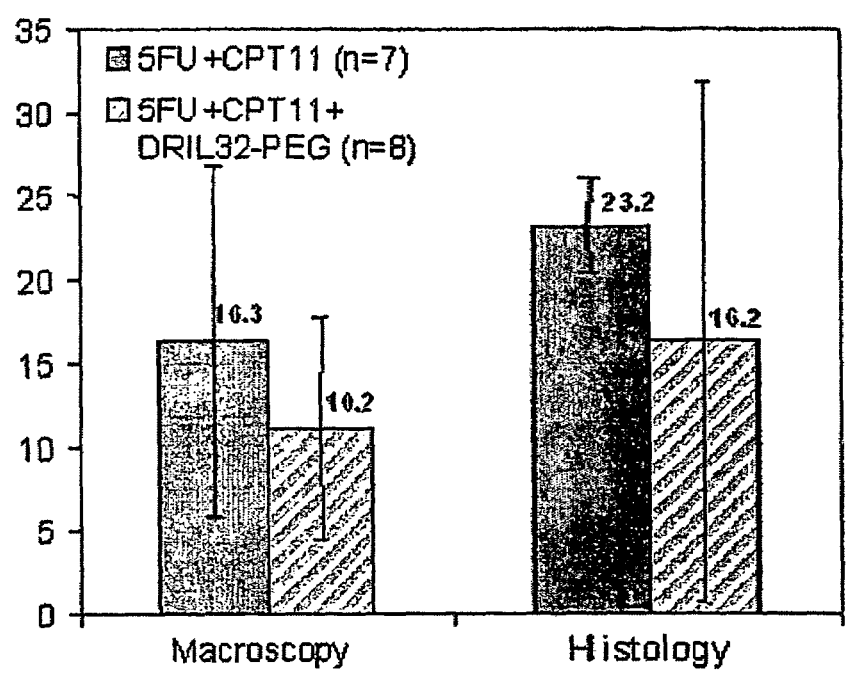
Figure 5.2

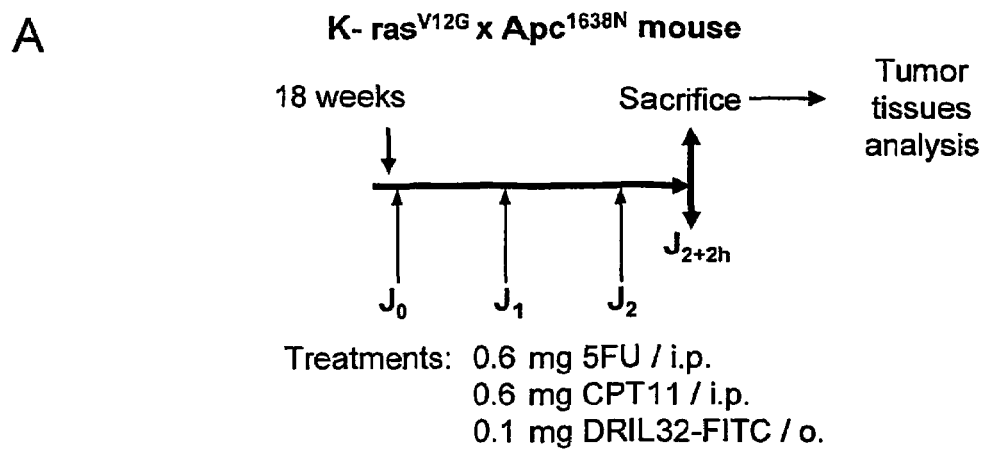
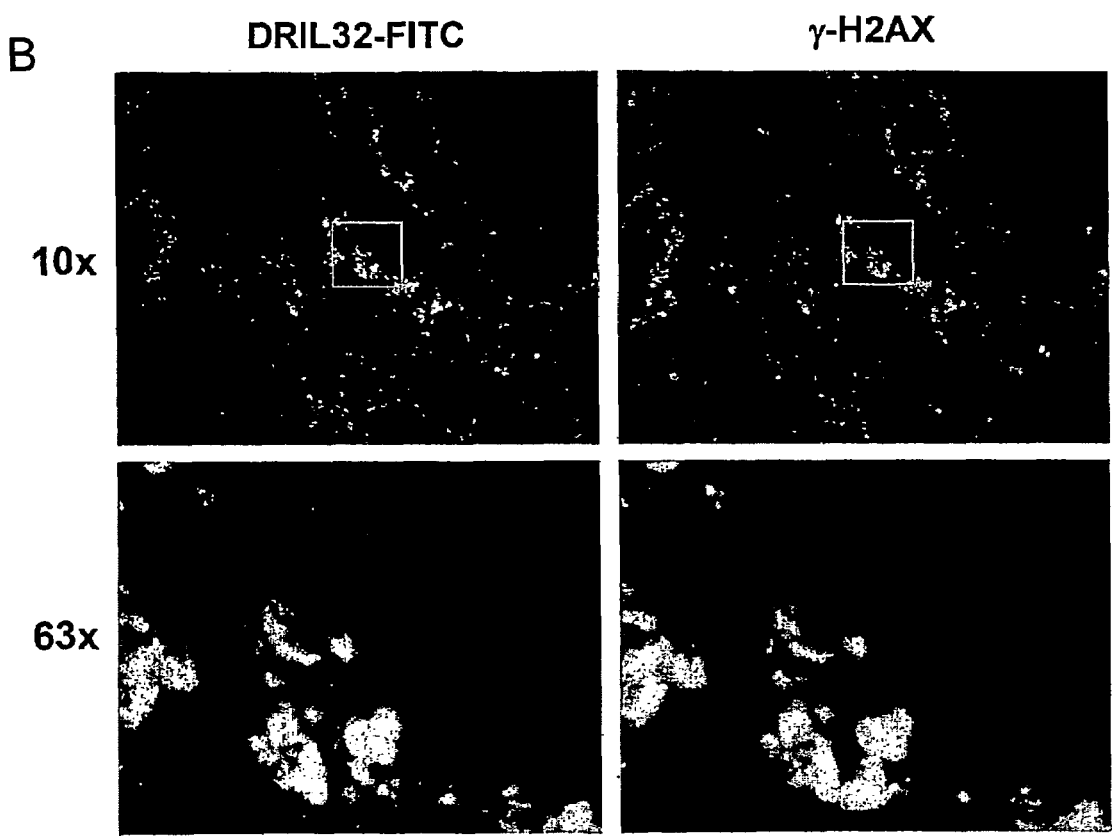
Figure 5.3.

SEQUENCE LISTING

<160> NUMBER OF SEQ ID NOS: 14

<210> SEQ ID NO 1
<211> LENGTH: 32
<212> TYPE: DNA
<213> ORGANISM: Artificial
<220> FEATURE:
<223> OTHER INFORMATION: DRIL

<400> SEQUENCE: 1
acgcacgggt gttgggtcgt ttgttcggat ct                32

<210> SEQ ID NO 2
<211> LENGTH: 32
<212> TYPE: DNA
<213> ORGANISM: Artificial
<220> FEATURE:
<223> OTHER INFORMATION: DRIL

<400> SEQUENCE: 2
acgcacgggt gttgggtcgt ttgttcggat ct                32

<210> SEQ ID NO 3
<211> LENGTH: 32
<212> TYPE: DNA
<213> ORGANISM: Artificial
<220> FEATURE:
<223> OTHER INFORMATION: DRIL

<400> SEQUENCE: 3
acgcacgggt gttgggtcgt ttgttcggat ct                32

<210> SEQ ID NO 4
<211> LENGTH: 24
<212> TYPE: DNA
<213> ORGANISM: Artificial
<220> FEATURE:
<223> OTHER INFORMATION: DRIL

<400> SEQUENCE: 4
acgcacgggt gttgggtcgt ttgt                         24

<210> SEQ ID NO 5
<211> LENGTH: 16
<212> TYPE: DNA
<213> ORGANISM: Artificial

```
<220> FEATURE:
<223> OTHER INFORMATION: DRIL

<400> SEQUENCE: 5
acgcacgggt gttggg                                                    16

<210> SEQ ID NO 6
<211> LENGTH: 8
<212> TYPE: DNA
<213> ORGANISM: Artificial
<220> FEATURE:
<223> OTHER INFORMATION: DRIL

<400> SEQUENCE: 6 acgcacgg                                                              8

<210> SEQ ID NO 7
<211> LENGTH: 32
<212> TYPE: DNA
<213> ORGANISM: Artificial
<220> FEATURE:
<223> OTHER INFORMATION: DRIL

<400> SEQUENCE: 7
acgcacgggt gttgggtcgt tgttcggat ct                                   32

<210> SEQ ID NO 8
<211> LENGTH: 32
<212> TYPE: DNA
<213> ORGANISM: Artificial
<220> FEATURE:
<223> OTHER INFORMATION: DRIL

<400> SEQUENCE: 8
acgcacgggt gttgggtcgt tgttcggat ct                                   32

<210> SEQ ID NO 9
<211> LENGTH: 32
<212> TYPE: DNA
<213> ORGANISM: Artificial
<220> FEATURE:
<223> OTHER INFORMATION: DRIL

<400> SEQUENCE: 9
acgcacgggt gttgggtcgt tgttcggat ct                                   32

<210> SEQ ID NO 10
<211> LENGTH: 32
<212> TYPE: DNA
<213> ORGANISM: Artificial
<220> FEATURE:
<223> OTHER INFORMATION: DRIL

<400> SEQUENCE: 10
gctaggcttg tttgctgggt tgtaggcaca gc                                  32

<210> SEQ ID NO 11
<211> LENGTH: 32
<212> TYPE: DNA
<213> ORGANISM: Artificial
<220> FEATURE:
<223> OTHER INFORMATION: DRIL

<400> SEQUENCE: 11
acgcacgggt gttgggtcgt tgttcggat ct                                   32
```

```
<210> SEQ ID NO 12
<211> LENGTH: 32
<212> TYPE: DNA
<213> ORGANISM: Artificial
<220> FEATURE:
<223> OTHER INFORMATION: DRIL

<400> SEQUENCE: 12
acgcacgggt gttgggtcgt ttgttcggat ct                              32

<210> SEQ ID NO 13
<211> LENGTH: 64
<212> TYPE: DNA
<213> ORGANISM: Artificial
<220> FEATURE:
<223> OTHER INFORMATION: DRIL

<400> SEQUENCE: 13
acgcacgggt gttgggtcgt ttgttcggat ctacgcacgg tcgtttgttc ggtgttggcg    60
atct                                                                64

<210> SEQ ID NO 14
<211> LENGTH: 64
<212> TYPE: DNA
<213> ORGANISM: Artificial
<220> FEATURE:
<223> OTHER INFORMATION: DRIL

<400> SEQUENCE: 14
acgcacgggt gttgggtcgt ttgttcggat ctacgcacgg tcgtttgttc ggtgttggcg    60
atct                                                                64
```

NUCLEIC ACIDS USEFUL FOR TRIGGERING TUMOR CELL LETHALITY

This application is the US national phase of international application PCT/EP2004/012857, filed 25 Oct. 2004, which designated the U.S. and claims priority of EP 03292666.9, filed 24 Oct. 2003, the entire contents of each of which are hereby incorporated by reference.

This invention is generally in the field of the use of oligonucletides/DNA fragements for biological and therapeutical applications, and more specifically in the field of nucleic acids that interfere with DNA damage signaling and repair pathways, in particular the non-homologous end jointing (NHEJ) pathway of double-stranded break (DSB) repair.

The invention relates to nucleic acids useful as tools for triggering cell lethality of tumors submitted to anticancer therapies.

Radiotherapy, chemotherapy, alone or combined together with surgery, are essential therapeutic arsenals against human cancer.

Ionizing radiations cause directly or indirectly double-strand DNA breaks (DSBs) and trigger cell/tissue death (necrosis or apoptosis). The cytotoxic effect of ionizing radiation forms the basis for radiation therapy, which is widely used in the treatment of human cancer. The efficacy of radiation therapy is currently limited by the radiation resistance of certain tumors (for example, glioblastomas) and by the side effects caused by irradiation of nearby normal tissues (for example, in treatment of breast and cervical cancer).

In the past years, many studies have focused on biological mechanisms related to the ionizing radiation response, in order to gain insights into the complexity of phenomena underlying radio-sensitivy or radio-resistance of tumor cells. The understanding of the different pathways which finely regulate the response to ionizing radiation is an important step towards the identification of molecular targets for new drugs and therapies that, in association with radiotherapy, could improve the chance of recovery from tumors highly resistant to radiation, such as brain or head and neck tumors.

The use of chemotherapeutic agents can cause DNA damages, including direct or indirect DSBs. Examples of mostly used families of chemotherapeutic agents (chemical cytotoxics) are: inhibitors of topoisomerases I or II (camptothecin/topotecan, epirubicin/etoposide), DNA crosslinkers (cisplatin/carboplatin /oxaliplatin), DNA alkylating agents (carmustine/dacarbazine) or anti-metabolic agents (5-fluorouracil/gemcitabine/capecitabine), as well as inhibitors of the mitotic spindles (paclitaxel/docetaxel/vinorelbine). Recent progress in developing biological cytotoxics (monoclonal antibodies, cytokines/kinase inhibitors, immunotherapies/vaccins) has proven their efficiency et specificity toward a subset of tumors. But they are often used in combination with chemical cytotoxics. Despites of many progress in the developments of new cytotoxic drugs, the drug resistance to chemotherapy is still a major clinical concern in the treatment of cancers. The understanding of the mechanism of drug resistance related to drug uptake/efflux, metabolic degradation, mutagenesis of target, enhanced repair, signaling of cell death (apoptosis and necrosis) is essential for insuring efficiency of chemotherapy and improve therapeutic index, especially, in some treatment-resistant tumors.

The association between chemotherapy and radiotherapy is widely used in the treatment of cancers. Although still not completely elucidated, the biological basis of action of the cytotoxics relies on cellular mechanisms, such as cell cycle or DNA damage, which are also important factors for the radio-induced cell death, leading to the additive or even better synergistic benefits by combining different treatments in cancer therapies.

In the last decade, many investigations were carried out in this field. The complexity of signal transduction in response to radiation began to be delineated.

Among the genes of particular interest to be targeted with ionizing radiations are those involved in the regulation of radiation-induced lethality mechanisms, such as apoptosis or DNA repair. Cell death induced by ionizing radiation depends mostly on the repair of DSBs.

Two mechanisms are involved in the repair of these lesions: non homologous end-joining (NHEJ, sequence-independent pathway) and homologous recombination (HR, sequence-dependent pathway) (reviewed by Jackson, 2002). Targeting genes involved in these two main DSB repair pathways leads to little or moderate radiosensitivity depending on the used approaches and cancer cell lines (Belenkov et al., 2002; Marangoni et al. 2000; Ohnishi et al., 1998).

Ku70 and Ku80, DNA-PKsc proteins are important in the repair of radiation- or chemo-induced DNA damage. If damage cannot be repaired on time, cells die. Therefore, they are interesting molecular targets for sensitizing target cells and tissues to radiotherapy and chemotherapy. Many approaches have been conceived and carried out to inhibit these key proteins (Ku70/Ku80, DNA-PKsc, etc.) involved in the NHEJ pathway which is considered as predominant in mammalian cells:

1) Inhibitors of PI3K (phosphatidylinositol-3-kinase) (i.e. DNA-PKsc, PARP-1, ATM, ATR) (Boulton et al., 2000; Durant & Karran, 2003; Willmore et al., 2004; Vauger et al., 2004)
2) Negative dominant & peptides (C-terminal of KU80) (Marangoni et al., 2000; Kim et al., 2002)
3) Single chain antibody variable fragment (scFv) (DNA-PKsc) (Li et al. 2003)
4) RNA Aptamer (SELEX: RNA binding Ku) (Yoo & Dynan, 1998)
5) Antisense (Ku70, Ku80, DNA-PKsc) (Li et al., 2003b; Marangoni et al., 2000; Sak et al., 2002)
6) siRNA (DNA-PKsc) (Peng et al. 2000).

Despite these tremendous efforts, the combination of DNA repair gene targeting and cancer therapies is still in early experimental stages and no clinical study has been shown any proven benefits so far. It is worth to note that the above described approaches share a common feature: they target a single effecter (protein) involved in a complex cascade pathway (such as NHEJ) with possible bypass.

The inventors have found that the tumor sensitivity to direct or indirect DNA damaging anticancer therapies can be enhanced by using chemically modified or not double-stranded nucleic acid molecules, acting as mimetics of broken DNA fragments and recognized as DSB sites induced by the DNA damaging treatments. The molecules may have a non replicative structure due said modifications.

An object of the invention is then to provide such double-stranded nucleic acid fragments, also named "DNA repair induced lethality" (DRIL in short) molecules in the following, capable of enhancing the response of treatment-resistant tumors to radiotherapy and chemotherapy.

More particularly, the invention aims at providing new DRIL molecules to be used in combination with physical and chemical agent (s) which can cause directly or indirectly DSBs of DNA and a method for treating cancer combining the use of said DRIL molecules with anticancer therapies which cause direct or indirect DNA damage.

Another object of the invention relates to the use of DRIL molecules for making anti-tumoral therapeutic adjuvant for enhancing efficiency of cancer treatment, particularly for highly resistant tumors to radio-and/or chemotherapies.

The DRIL molecules of the invention are substrates for proteins involved in the NHEJ pathway (sequence-independent pathway), particularly Ku proteins and comprise a sequence-independent backbone of at least 4-10000 base pairs (bp), particularly 4-1000 bp.

They are Such that
- the double-stranded DRIL molecules are capable of being uptaken by cell/tissue body into the cell nucleus when used with pharmaceutically acceptable carriers;
- the free ends of the DRIL molecules are recognizable by the DNA binding proteins involved in double-strand breaks repair and damaging signalling,
- the free ends of the DRIL molecules is amenable by said enzymes to be incorporated in the tumoral cell genomic DNA.

According to the mechanism of action of DRIL molecules via NHEJ pathway, their length are not a limitation per se, except for practical considerations, but must include at least 4 bp, more preferably at least 8 bp.

Preferably, the DRIL molecules of the invention then comprise 8-500 bp, and most preferably 16-200 bp.

Particularly preferred DRIL molecules comprise 16-100 bp, and more advantageously 24-100 bp.

The DRIL molecules according to the invention have a native phosphodiester backbone or a chemically modified phosphodiester backbone, or another backbone with chemical groups or mixtures of chemical groups, provided the modified oligomers remain substrates for proteins involved in the NHEJ pathway, particularly Ku proteins, and DSB damage signalling pathway. Advantageously, the chemical modifications are intended to confer chemical stability to DRIL molecules and/or to prevent them for further replication (potential cause of mutagenic effect) upon their genomic integration if it occurs.

They can also have sugar mimetics such as 2'-O-alkylribose, 2'-O-alkyl-C4' branched ribose, cyclobutyls or other carbocyclics or hexitol in place of the pentofuranosyl group.

They can be made linear or made of hairpin double-stranded nucleic acids in which the loop can be nucleic acids, or other chemical groups known by skilled person, preferably a linker such as hexaethyleneglycol or tetradeoxythymidylate (T4).

DRIL molecules of the invention can be made of at least one free dsDNA end; said free end may be blunt or 5'-/3'-protruding end and comprise modified nucleic acid backbones or other chemical groups or mixture of chemical groups known by skilled person.

Preferred fragments comprise one or several chemical groups at the end of each strand. Preferred chemical groups comprise phosphorothioates. Alternatively, preferred fragments have 3'-3' nucleotide linkage.

Other modified backbones of the invention comprise methylphosphonates, phosphoramidates, morpholino nucleic acid, 2'-O, 4'-C methylene/ethylene bridged locked nucleic acid, peptide nucleic acid (PNA), and short chain alkyl, or cycloalkyl intersugar linkages or short chain heteroatomic or heterocyclic intrasugar linkages of variable length, or any modified nucleotides known by skilled person.

U.S. Pat. No. 5,677,437 describes heteroaromatic oligonucleoside linkages. Nitrogen linkers or groups containing nitrogen can also be used to prepare oligonucleotide mimics (U.S. Pat. No. 5,792,844 and No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phophodiester backbone of the oligonucleotide may be replaced with a polyamide backbone, the bases being bound directly or indirectly to the aza nitrogen atoms of the polyamide backbone. Other synthetic oligonucleotides may contain substituted sugar moieties comprising one of the following at the 2' position: OH, SH, $OCH_3$, $SCH_3$, F, OCN, $OCH_2CH_2OCH_3$, $O(CH_2)_n NH_2$ or $O(CH_2)_n CH_3$ where n is from 1 to about 10; C1 to C10 lower alkyl, substituted lower alkyl, alkaryl or aralkyl; Cl; Br; CN; $CF_3$; $OCF_3$; O-; S-; or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylyamino; substituted silyl; or a group for improving the pharmacokinetic and/or pharmacodynamic properties of an oligonucleotide, and other substitutents having similar properties.

The DRIL molecules are essentially based on natural nucleotides either 2'-deoxynucleotides or 2'-ribonucleotides and optionally comprise one or several modified nucleotides and/or nucleobases other than adenine, cytosine, guanine, thymine and uracil.

Appropriate nucleobases other than the usual bases are for example C5-methylcytosine, uracile, pseudoisocytosine, C5-propynyluracil, N7-deazaguanine, N7-glycosylated guanine, or alpha anomer, or other modified nucleobases or a basic residue.

The chemically modified DRIL molecules, which will be in the cell in the tissue or in the body when they are irradiated or treated by chemotherapies, will be either incorporated into genomic DNA at the DSB sites, or recognized as DSB sites induced by ionizing radiation by cellular DNA repair mechanism as NHEJ. Then, they will be bound by DSB repair proteins, either being integrated into the broken chromosomes or saturating the repair system.

According to an embodiment of the invention, said DRIL molecules further comprise at least one embedded element which hampers DNA replication, DNA repair, or damage signalling process.

Said non-replicable element(s) can be incorporated at the internal position or at the end of the double-stranded fragment. It (they) may comprise:
- a) a unit which cannot be used as a template for DNA replication, such as a polyethyleneglycol chain, preferably a hexaethyleneglycol chain, or any hydrocarbon chain, eventually interrupted and/or substituted by one or more heteroatoms e.g. oxygen, sulfur, nitrogen, or heteroatomic or heterocyclic groups comprising one or more of heteroatoms;
- b) a unit which is a blocking element as it is not amenable by DNA polymerases or exonucleases, such as any 3'-modified nucleotides, or other ones known by skilled person;
- c) a native oligonucleotide, such as $T_n$, when used in the loop of an hairpin fragment, preferably a tetradeoxythymidylate (T4).

Said strands are made by chemical synthesis, semi-biosynthesis or biosynthesis, any method of amplification, followed by any extraction and preparation methods and any chemical modification.

The experiments carried out in cultured cells and in xenografted tumors on nude mice and genetically modified mice have shown that said DRIL molecules trigger cell/tissue lethality of tumors submitted to a radio-and/or chemotherapy.

The invention thus also relates to adjuvant compositions to be used in association with a DNA breaking treatment, said compositions comprising a DRIL molecule such as above defined, in combination with a pharmaceutically acceptable carrier, in an efficient amount to be introduced in the nucleus of tumoral cells.

The invention also relates to a method for promoting tumor sensibility to anticancer therapies which comprises, in association,
- introducing into cancer cell/tissue DRIL molecules such as above defined, and
- inducing in cells, DNA breakage by a DNA damaging method.

According to an embodiment of the invention, a transfection agent is used in said introduction step.

Based on the protocol used in in vivo studies, the invention provides rational to establish clinical protocol of the use of DRIL molecules in combination with radiotherapy or chemotherapy. The rational underlying any protocol is that the DRIL molecules should be delivered in the nucleus of cells when DNA damaging event occurs. Therefore, DRIL molecules must to be administrated several hours prior radiotherapy, whereas they can be given along with chemotherapeutic agent(s) depending on the administration mode and the pharmacokinetics of each component.

The protocol on mice comprises administration of DRIL molecules several hours before irradiation, for example 5 hours, and 3 times a week, a total dose of irradiation corresponding to 30 Gy over 6 weeks of treatments. The use of a fractionated irradiation is particularly efficient.

Advantageously, said method comprises coupling the treatment with DRIL molecules with a double chemotherapy. For example 5-FU and CPT 11 are injected together 3 times, 3 consecutive days, spaced by a full week of rest. Alternatively the treatment with DRIL molecules is coupled with radiotherapy.

It will be easily adapted for humans by the one skilled in the art, particularly depending on the weight of the patient.

In a preferred embodiment, the DRIL molecules are chemically modified DRIL molecules such as above defined and other practice in human therapy.

In another embodiment, the DRIL molecules are not chemically modified and correspond to native nucleic acid fragments, but exhibit the characteristics of chemically modified fragments, particularly have the number of base pairs and properties defined with respect to said chemically modified DRIL molecules.

More particularly DNA strand breakage is achieved by ionized radiation (radiotherapy) or chemical reaction (chemotherapy).

Such a method is a new therapeutic adjuvant in conjunction with DNA damaging therapies to tumors.

The invention also relates to the use of said non-chemically modified DRIL molecules for making anti-tumoral drugs for treating tumors, particularly highly resistant tumors to radio- and/or chemotherapies, said drugs being used in association with a DNA breaking treatment, particularly radiotherapy or chemotherapy.

In vivo, the chemically modified or non-modified DRIL molecules are administrated by any appropriate route, with appropriate acceptable carrier, such as oral, or intravenous, or intratumoral administration, or sub-cutaneous injections, or others.

Others characteristics and advantages of the invention will be given in the following examples, with reference to FIGS. 1 to 5, and Tables 1 and 2, said figures representing, respectively:

FIG. 1.1: Band-shift assays performed on different $^{32}$P radiolabeled DRIL molecules in the presence of various amounts of nuclear extract from Hep2 cells;

FIG. 1.2: Identification of the presence of Ku proteins in the retarded bands of different $^{32}$P radio-labelled DRIL molecules involving proteins in Hep2 cell nuclear extract;

FIG. 2.1: Clonogenic survival assay of Hela cells after irradiation performed with γ-rays of DRIL molecules);

FIG. 2.2: Inhibition of radiation-enhanced illegitimate integration of a linear plasmid fragment (2 µg) carrying the gene coding for neomycin resistance by DRIL32-PEG molecules;

FIG. 2.3: Hela cells transfected by fluorescent DRIL32-FITC molecules after irradiation;

FIG. 3.1: FACS analyses of the untreated GMA32 cells, the cells transfected alone, or transfected with different DRIL molecules by lipofectamine, but without further irradiation or mitotic inhibitor treatment;

FIG. 3.2: Immunodetection of DNA repair foci by γ-H2AX labeling in the untreated GMA32 cells, the cells transfected alone, or transfected with different DRIL molecules by lipofectamine;

FIG. 3.3: Western blot analysis of the phosphorylation status of p53 serine 15 residue of the untreated GMA32 cells, the cells transfected alone, or transfected with different DRIL molecules by lipofectamine, but without further irradiation or mitotic inhibitor treatment.

FIG. 3.4: Clonogenical survival of untreated and treated GMA32 cells by irradiation or by different mitotic inhibitors;

FIG. 4: Growth of the xenografted human larynx tumor on mice monitored as the ratio of the tumor volume at time t over the initial volume ($V_t/V_i$) with or without treatments;

FIG. 5.1: Chemosensitization of the treatment of digestive tumors induced in K-Ras$^{V12G}$×Apc$^{1638N}$ transgenic mice; and FIG. 5.2: Mean number of digestive tumors per animal by macroscopy or histology examination.

FIG. 5.3: Panel A: Protocol schema (i.p.: intraperitoneal injection; o.: oral administration). Panel B: Fluorescence of DRIL32-FITC (left) and of immunofluorescence labelled γ-H2AX (right) on the 5 µm section from the tumor tissue of the treated animal according to the protocol given in panel A. Lower parts show the details (using 63× lens) of the indicated zone in the upper parts (using 10× lens, white box). Colocalization of fluorescentDRIL32-FITC and labelled γ-H2AX appears as bright dots over DAPI counterstained nuclei. Color pictures are available upon request.

Molecular and cellular studies as well as assays in xenografted human radio-resistant tumor (head & neck, glioblastoma) on nude mice and in Ras$^{V12G}$×Apc$^{163N}$ double mutation induced tumor in digestive track on transgenic mice were performed in order to: i) assess the biological activities of DRIL molecules; ii) validate DNA Bait approach by using DRIL molecules in sensitizing anticancer therapies; iii) elucidate molecular and cellular mechanisms underlying the observed DRIL effects. The outcomes of these investigations are outlined and summarized in the following sections (examples):

EXAMPLE 1

Design, Synthesis and Preparation of DRIL Molecules

Two types of DRIL molecules were designed: linear or hairpin dsDNA fragments. For hairpin DRIL molecules, a hexaethyleneglycol linker (abbreviated as PEG) or a tetradeoxythymydylate (abbreviated as T4) was used as loop. The end(s) of dsDNA stem can be protected against chemical degradation by 3'-exonucleases by incorporation of phosphorothioates, or 3'-3' nucleotide linkage. In principle, other chemical modifications can be used provided that they are compatible with Ku70/Ku80-DNA PKsc binding (Martensson & Hammarten, 2002). Different DRIL molecules with various stem length 8 bp (DRIL8-PEG), 16 bp (DRIL16-PEG), 24 bp (DRIL24-PEG) and 32 bp (DRIL32-PEG), as well as different stem sequences were used. A dumbell dsDNA fragment (DRIL32-2×PEG) where both ends were sealed by two PEG loops was also designed, as control. Some DRIL molecules were labelled via a T tagged with fluorescein (DRIL32-FITC), cyanine 3 (DRIL32-Cy3), or biotin (DRIL32-Bt). Table 1.1 and 1.2 summarized the sequences and chemical structures of DRIL molecules used in this work.

TABLE 1.1

Sequences and chemical structures of DRIL molecules. The Bold letters are nucleotides with phosphorothioate backbone. Solid line symbolizes hexaethyleneglycol linker (PEG). DRIL32-T4 contains $T_4$ as a linker instead of PEG linker. DRIL32-2xPEG is a dumbbell (closed) molecule. DRIL32s33-PEG has a shuffled sequence (same base composition but in different order) and a 3'-3' linkage.

| DRIL molecules | Sequences and chemical structures |
|---|---|
| DRIL32 (SEQ ID NO:1) | 5'ACGCACGGGTGTTGGGTCGTTTGTTCGGATCT3'<br>3'TGCGTGCCCACAACCCAGCAAACAAGCCTAGA5' |
| DRIL32po-PEG (SEQ ID NO:1) | 5'ACGCACGGGTGTTGGGTCGTTTGTTCGGATCT3'<br>3'TGCGTGCCCACAACCCAGCAAACAAGCCTAGA5' |
| DRIL32-PEG (SEQ ID NO:1) | 5'ACGCACGGGTGTTGGGTCGTTTGTTCGGATCT3'<br>3'TGCGTGCCCACAACCCAGCAAACAAGCCTAGA5' |
| DRIL24-PEG (SEQ ID NO:2) | 5'ACGCACGGGTGTTGGGTCGTTTGT3'<br>3'TGCGTGCCCACAACCCAGCAAACA5' |
| DRIL16-PEG (SEQ ID NO:3) | 5'ACGCACGGGTGTTGGG3'<br>3'TGCGTGCCCACAACCC5' |
| DRIL8-PEG (SEQ ID NO:4) | 5'ACGCACGG3'<br>3'TGCGTGCC5' |
| DRIL32ss (SEQ ID NO:1) | 5'ACGCACGGGTGTTGGGTCGTTTGTTCGGATCT-3' |
| DRIL32-T4 (SEQ ID NO:1) | 5'ACGCACGGGTGTTGGGTCGTTTGTTCGGATCT3'  $T_4$<br>3'TGCGTGCCCACAACCCAGCAAACAAGCCTAGA5' |
| DRIL32-2 × PEG (SEQ ID NO:1) | 5'ACGCACGGGTGTTGGGTCGTTTGTTCGGATCT3'<br>3'TGCGTGCCCACAACCCAGCAAACAAGCCTAGA5' |
| DRIL32s33-PEG (SEQ ID NO:5) | 5'GCTAGGCTTGTTTGCTGGGTTGTAGGCACAGC3'<br>5'C3'-3'GATCCGAACAAACGACCCAACATCCGTGTCG5' |

TABLE 1.1-continued

Sequences and chemical structures of DRIL molecules. The Bold letters are nucleotides with phosphorothioate backbone. Solid line symbolizes hexaethyleneglycol linker (PEG). DRIL32-T4 contains $T_4$ as a linker instead of PEG linker. DRIL32-2xPEG is a dumbbell (closed) molecule. DRIL32s33-PEG has a shuffled sequence (same base composition but in different order) and a 3'-3' linkage.

| DRIL molecules | Sequences and chemical structures |
|---|---|
| DRIL32-NH2 (SEQ ID NO:1) | 5'ACGCACGGGTGTTGGGTCGTTTGTTCGGATCT3'-NH$_2$<br>3'TGCGTGCCCACAACCCAGCAAACAAGCCTAGA5'-NH$_2$ |
| DRIL32-FITC<br>DRIL32-Cy3<br>DRIL32-Bt (SEQ ID NO:1) | 5'ACGCACGGGTGTTGGGTCGTTTGTTCGGATCt3'<br>3'TGCGTGCCCACAACCCAGCAAACAAGCCTAGA5' | t = fluorescein (FITC), cyanine 3 (Cy3) or biotin (Bt)-tagged T

TABLE 1.2

Sequences and chemical structures of 64-bp DRIL molecules. The Bold letters are nucleotides with phosphorothioate backbone. Solid line symbolizes hexaethyleneglycol linker (PEG).

| DRIL molecules | Sequences and chemical structures |
|---|---|
| DRIL64 (SEQ ID NO:6) | 5'ACGCACGGGTGTTGGGTCGTTTGTTCGGATCTAC GCACGGTCGTTTGTTCGGTGTTGGCGATCT3'<br><br>3'TGCGTGCCCACAACCCAGCAAACAAGCCTAGATG CGTGCCAGCAAACAAGCCACAACCGCTAGA5' |
| DRIL64-PEG (SEQ ID NO:6) | 5'ACGCACGGGTGTTGGGTCGTTTGTTCGGATCT-ACGCACGGTCGTTTGTTCGGTGTTGGCGATCT3'<br><br>3'TGCGTGCCCACAACCCAGCAAACAAGCCTAGA-TGCGTGCCAGCAAACAAGCCACAACCGCTAGA5' |

All DRIL molecules were made by automated solid phase oligonucleotide synthesis (Eurogentec, Belgium). They were purified by denaturing reverse phase HPLC. Denaturing capillary gel electrophoresis and MALDI-TOF/LC-MS were used for quality control. More than 90% of oligonucleotides are full length. All samples were lyophilized before shipping.

Upon reception, all samples were dissolved in bi-distilled water. The concentrations of unlabelled DRIL molecules were measured by spectrophotometry (Cantor & Warshaw, 1970) under denaturing condition (60° C.-90° C. depending on the thermal stability of DRIL molecules). The dumbell dsDNA fragment (DRIL32-2×PEG) was prepared by annealing and ligation by DNA T4 ligase (BioLabs) of two semi hairpins carrying PEG loop and with 3' protruding and complementary ends.

Based on the thermodynamic and kinetic considerations, the following protocols were used for preparing the samples of DRIL molecules, according to their molecularity:

For Bi-Molecular DRIL Molecules (DRIL32, DRIL64 and DRIL64-PEG):

The mixture of 1:1 stock solution (highest concentration possible) of each strand in bi-distilled water has to be heated at 90° C. for 5 minutes for complete denaturation of each strand. The annealing was carried out by smooth return to room temperature (the samples are typically left in water bath) and the resulting duplex molecules were stored in aliquot at −20° C.

For mono-molecular DRIL molecules (hairpin):
The solution containing 200 μM of hairpin DRIL molecules in bi-distilled water has to be heated at 90° C. for 5 minutes for complete denaturation. The annealing has to be carried out by chilling the samples into ice-water (0° C.). Storage of aliquots was at −20° C.

EXAMPLE 2

Biochemical Analysis of DRIL Molecules

As the first step to dissect the mechanism of action of DRIL molecules, a series of band-shift assays were carried out with different $^{32}$P radio-labelled DRIL molecules in the presence of nuclear protein extracts from Hep2 cells according to standard protocol. Typically, 10 nM $^{32}$P radio-labelled DRIL molecules were incubated in the presence of various concentrations of nuclear proteins (0, 10, 20, 40, 80, 160, and 320 ng/μl) at 30° C. for 10 minutes in TBE buffer. Then the samples were loaded on a 5% acrylamide native gel. The electrophoresis was run at 95V for 2 hours at 4° C. The gel was dried and scanned by phosphorimager (Molecular Dynamics).

FIG. 1.1 shows that, except the 8-bp DRIL8-PEG molecules (the shortest DRIL molecule), up to 3 retarded bands were observed for longer DRIL molecules with a common band (band 1). Other bands occurred in the presence of long DRIL molecules. The retarded band pattern of the titration of Hep2 nuclear protein extracts with 32-bp long DRIL molecules (DRIL32-PEG, DRIL32po-PEG and DRIL32) is more complex. The intensity of the retarded band 1 increases and then decreases as the concentration of protein increases. The intensity of the retarded bands 2 and 3 increases as a function of protein concentration until it reaches a plateau.

Performing binding interactions and band-shift assays with mouse monoclonal anti-Ku70 antibody (Santa Cruz Biotechnology) revealed that retarded bands 1 and 2 contain the Ku complex (FIG. 1.2: On line α-Ku, it is indicated when anti-Ku antibodies were added (+) or not (−) to the binding reaction before loading of sample on the gel. The bands were numbered 1, 2 and 3 and a star was added to number for bands showing a shifted migration after anti-Ku binding).

Band 1 and 2 are super-shifted into band 1* and 2* upon anti-Ku70 antibody addition. It is likely that band 1 has one Ku70/80 complex bound to the DRIL and band 2 two Ku70/80 complexes bound to the DRIL. Control experiments performed with purified Ku proteins confirmed this interpretation. It is noted that the band 3 disappeared upon addition of anti-Ku70 antibody (clearly seen with DRIL24-PEG and DRIL32po-PEG), showing that the band 3 also contains the Ku complex.

The identification of Ku proteins clearly indicates that DRIL molecules interact with NHEJ machinery.

EXAMPLE 3

In Vitro Activity of DRIL Molecules

The activity of DRIL molecules in cultured cells was studied by clonogenic survival assay in two radio-resistant human cancer cell lines derived from a female cervix carcinoma (HeLa) and from carcinoma of larynx (Hep2) in association with ionizing radiation.

3.1) Induced Cell Lethality

Upon 8 hours transfection of DRIL molecules in Hela cells and four irradiation with 0.5 Gy split doses spaced 2 hours (4×0.5 Gy), performed with □-rays from a $^{137}$Cesium, a significant reduction of clonogenic survival was observed as compared to untransfected cells. The results are given on FIG. 2.1 wherein Panel A gives the dose-dependence of normalized survival clone number in the presence of DRIL32 and DRIL32-PEG, and Panel B, the normalized survival clone number in the presence of different DRIL molecules at 83 nM (concentration in culture medium).

The effect depends on the chemical nature of DRIL molecules in a dose-dependent manner. In this assay, the hairpin DRIL molecules (DRIL32-PEG, DRIL32-T4 and DRIL24-PEG) and the linear double-stranded DRIL molecules (DRIL64-PEG and DRIL64) significantly reduced clonogenic survival. It is worth to note that the dumbell DRIL molecule (DRIL32-2×PEG) which lacks free dsDNA ends (capped by hexaethyleneglycol linker at both ends) did not exhibit any effect. The chemical nature of loop did not matter (for example, DRIL32-PEG versus DRIL32-T4). These observations indicate that some of the DRIL molecules can sensitize cells to ionizing radiation.

Cell culture was in MEM supplemented with 10% serum. Superfect (Qiagene) was used as transfection agent according to the manufacturer's instruction. Clonogenic survival was estimated as the number of treated cells forming colonies on the number of untreated cells.

3.2) Inhibition of Illegitimate Integration of Exogenous DNA by DRIL Molecules

Ionizing radiation is known to improve transfection of exogenous DNA, a process termed radiation-enhanced integration. Hela cell culture was used for this assay. Cells were transfected during 8 hours by 2 μg of a linear plasmid (carrying the gene coding for neomycin resistance) and three different ratio of DNA/superfect (1:2, 1:5, 1:10). During transfection time, the cells were exposed to different irradiation protocols: no irradiation, one single irradiation of 1 Gy and 2 Gy, as well as a 2 Gy irradiation delivered by split doses of 0.5 Gy every 2 hours (4×0.5 Gy). Integration of the plasmid was monitored by selection of Neo$^R$ cells growing in a medium containing 0.6 mg/ml of G418. Plasmid integration was significantly enhanced by the split irradiation protocol. When 2 μg of DRIL32-PEG molecules were added to the transfection mix, the radiation-enhanced integration was abolished (FIG. 2.2).

This experiment showed that the radiation-enhanced illegitimate integration of exogeneous DNA which required Ku, DNA-PK and ATM proteins (Nimura et al., 2002) is inhibited by DRIL molecules as expected, as the mechanism of action of the DRIL32-PEG molecules act through the trapping of the proteins involved in a NHEJ pathway.

3.3) Induced Inhibition of DSBs Repair

DSB damages in nuclei can be immunodetected by using γ-H2AX antibody which labels DNA breaks. Most of the H2AX foci appear rapidly after irradiation and disappeared as DSBs repair process progressed. Few H2AX foci were detected two hours after irradaiation in non transfected cells.

FIG. 2.3 gives the results obtained with Hela cells transfected by fluorescent DRIL32-FITC molecules at 2 hours after 2 Gy irradiation. Left panel: fluorescence of DRIL32-FITC (bright dots and patches) and DNA repair-foci detected by immunofluorescence of γ-H2AX antibody in nuclei; Right panel: the same image of nuclei with DNA repair foci detected by immunofluorescence of γ-H2AX antibody and DAPI counterstaining. The arrows at the lower left corner show the absence of DRIL32-FITC and γ-H2AX signal in nucleus. The arrows at the upper right corner show the co-localized DRIL32-FITC and γ-H2AX signals.

As shown on FIG. 2.3, unrepaired DSB breaks persisted in Hela cells transfected by DRIL32-FITC molecules two hours after irradiation (2 Gy), as shown by double fluorescent labelling with DRIL32-FITC and that of γ-H2AX antibody. It is worth to note that in the same culture the DSB repair foci were almost undetectable in the cells that were not efficiently transfected by DRIL32-FITC, suggesting the DNA repair was complete in these cells.

Transfection and irradiation protocoles were similar to those described above. For immunodetection, the cells were grown on surface coverslip in 5 cm diameter Petri dishes, transfected with 2 μg DRIL32-FITC molecules labeled with FITC with Superfect (Qiagene) according to the manufacturer's instruction. Four hours after the beginning of the transfection, cells were irradiated (2 Gy), then rest for 2 hours in the medium at 37° C. After 3 washing cycles, the cells were fixated with 2% PFA for 10 minutes. After one additional washings, the presence of □-H2AX was detected with rabbit anti-□-H2AX antibody (4411-PC, Trevigen) diluted 1/100 in 1×PBS, 1% BSA. Cells were washed three times with 1×PBS, 0.5% TritonX-100, then incubated for 1 hour at room temperature with rhodamine-conjugated goat anti-rabbit antibodies diluted 1/100 in 1×PBS, 1% BSA. Cells were visualized by epifluorescence microscopy.

EXAMPLE 4

Effects of DRIL Molecules in GMA32 Cell Line and their Association with Irradiation or Mitotic Inhibitors The GMA32 Chinese hamster fibroblast cells permissive of DNA breaks were maintained in MEM medium (Gibco) supplemented with 1 mM sodium pyruvate, 2 mM glutamine, 1×MEM non essential amino acids, 1× penicillin/streptomycin and 10% horse serum. Typically, $2 \times 10^5$ to $4 \times 10^5$ cells were seeded in medium without antibiotics, in 5 cm diameter Petri dishes 24 hours before the transfection of different DRIL molecules (4.5 μg) with lipofectamine 2000 (LifeTechnologies) as transfection agent (in a 1:3 ratio), according to the manufacturer's instructions. At the end of the transfection the cells were either irradiated (4 Gy) or treated with mitotic inhibitors: nocodazole (200 nM), navelbine (100 nM) or taxol (200 nM). About 16 hour later the drug was removed and the cells were allowed to recover. Cell irradiation was performed with γ-rays from a $^{137}$Cesium source. After a 24 hour recovery, the cells were collected and used either for FACS, western blot analyses or to determine the clonogenicity (survival) and the effect of each treatment.

FIG. 3.1 shows FACS analyses of the untreated GMA32 cells, the cells transfected alone, or transfected with different DRIL molecules by lipofectamine, but without further irradiation or mitotic inhibitor treatment. The M1 phase represents the percentage of cells in sub-G1 stage indicative of cell death. Significant cell death was observed only in the presence of double-stranded DRIL32 and hairpin DRIL32-PEG molecules, whereas hairpin DRIL16-PEG and single-strand DRIL32ss induced intermediate and moderate cell death, respectively. The shortest hairpin DRIL8-PEG failed to trigger cell death as compared to the control (cells transfected by lipofectamine alone).

The experiments were performed with a FACScalibur flow cytometer (Becton Dickinson). Cells were collected, suspended in 1 ml of cold GM buffer (6.5 mM glucose, 137 mM NaCl, 5.4 mM KCl, 2 mM $Na_2HPO_4$, 1 mM $KHPO_4$, 0.5 mM EDTA), and stored at 4° C. for at least 2 hours after addition of 3 ml of cold 100% ethanol. At that stage, cells were eventually washed with 1×PBS, then stained for 30 minutes at room temperature in PI solution (50 μg/ml propidium iodide, 25 μg/ml RNase A in 1×PBS buffer). 10 000 events were analyzed with Cellquest software, and cell aggregates were gated out. The percentage of cells with a sub-G1 content of DNA was scored.

Under the same conditions, the immunodetection of DNA repair foci of H2AX phosphorylated on serine 139 by γ-H2AX labeling (bright dots or patches in nuclei) was performed in the untreated GMA32 cells, the cells transfected alone, or transfected with different DRIL molecules by lipofectamine. The counterstaining of cell membranes and nuclei were achieved by FITC-DiOC6 and DAPI. Similar effects of DRIL molecules were observed (FIG. 3.2). This experiment shows that both double-stranded DRIL32 and hairpin DRIL32-PEG can effectively trigger similar cell response as if DNA damages were occurred in nuclei. This provides visual evidence that these DRIL molecules can be used for trapping proteins involved in DSB repair via NHEJ pathway.

For immunodetection, the cells were grown on coverslip in 5 cm diameter Petri dishes 24 hours before the transfection with different DRIL molecules. One day after the transfection, FITC-DiOC$_6$ (Molecular probes) was added in the medium 5 minutes at 37° C. (to counterstain the membranes). After 3 washing cycles, the cells were fixated with 4% PFA for 20 minutes. After additionnal washings, H2AX phosphorylated on serine 139 (γ-H2AX) was detected with rabbit anti-γ-H2AX antibody (4411-PC, Trevigen) diluted 1/100 in 1×PBS, 1% BSA. Cells were washed three times with 1×PBS, 0.5% TritonX-100, then incubated for 1 hour at room temperature with goat anti-rabbit antibodies Alexa 594 (Molecular Probes) diluted 1/100 in 1×PBS, 1% BSA. Cells were visualized by epifluorescence microscopy.

Further experiment was carried out in order to look for evidence of DNA damage signaling. The protein p53 is a well known major protein in mediating DNA damage signaling and in coordinating appropriate responses (DNA repair, apoptosis, etc.) by changing its phosphorylation status. In particular, the phosphorylation of serine 15 residue is involved in the interaction with MDM2 protein which acts as a feed back control. Thus, the phosphorylation status of the serine 15 of p53 was assessed by Western blot. FIG. 3.3 shows that the p53 serine 15' was highly phosphorylated when cells were transfected by either double-stranded DRIL32 or hairpin DRIL32-PEG molecules, whereas the shorter hairpin DRIL16-PEG induced moderate phosphorylation. Neither the shortest DRIL8-PEG nor single strand DRIL32ss molecules were able to induced significant phosphorylation on the serine 15 of p53 protein. This experiment provides additional evidence that the presence of both double-stranded DRIL32 and hairpin DRIL32-PEG in GMA32 cells was detected as DNA damage and induced the signal to transducer responses such as p53 protein phosphorylation, likely through ATM activation pathway.

For Western blot analysis, cells were lysed in Laemmli buffer. Equal amounts of lysates were resolved in 12% polyacrylamide gels. Proteins were transferred to nitrocellulose membranes, which were blocked with 5% nonfat milk (1 hour) before overnight incubation with anti-p53Ser15 antibody (9284, Cell Signaling) diluted 500 times in TBST buffer (10 mM Tris-HCl pH7.5, 150 mM NaCl, 0.1% Tween 20) containing 5% nonfat milk. Blots were then incubated with horseradish peroxidase-conjugated goat anti-rabbit IgG secondary antibodies (PO448, Dako) diluted 1/5000 in TBST. Protein-antibody complexes were detected by enhanced chemiluminescence (RPN2106 ECL, Amersham).

The effect of radiosensitization and chemosensitization of DRIL molecules in GMA32 cells was evaluated by clonogenicity (clonal survival) assay. FIG. 3.4 shows that the radiosensitization to 4 Gy irradiation was observed in GMA32 cells transfected with either double-stranded DRIL32 or hairpin DRIL32-PEG molecules. In addition, the chemosensitization was also observed for GMA32 cells transfected with either double-stranded DRIL32 or hairpin DRIL32-PEG molecules when they were treated by mitotic inhibitors (200 nM nocodazole, 100 nM navelbine (vinorelbine) or 200 nM taxol (paclitaxel)). These drugs block either polymerization or depolymerization of microtubules, and can induce indirectly DNA breakage.

For the clonogenicity assay, serial dilutions were made after counting the cells to seed 5 cm Petri dishes with different amounts of cells. The number of cells range from 100-200 (control cells) to 3000 (transfected or/and treated cells). Ten days after, the cells (forming clone) were fixed with 4% paraformaldehyde (20 minutes), then colored with methylene blue (15 minutes), and the number of clone in each plate (in triplicates) was scored.

EXAMPLE 5

Radiosensitization of the Treatment of Xenografted Human Tumors on Nude Mice

In vivo activity of DRIL molecules in association with radiotherapy was assessed by using nude mice xenografted with human tumors by subcutaneous injection of radio-resistant cell lines (Hep2 derived from carcinoma of larynx) or tumor fragments (previously obtained by subcutaneous injection of the U87 cell lines derived of glioblastoma).

Investigations were mainly carried out on the mice xenografted with radio-resistant human larynx tumors in order to establish proof of concept in vivo. Irradiation was performed with γ-rays from a $^{137}$Cesium source with appropriate protection of mice in order to perform localized irradiation of tumors. Typical assay condition consists of intratumoral injection of an appropriate preparation of 1 nmole DRIL molecules with transfecting agents (cationic dendrimer (Superefct, Qiagene), dioctadecylamidoglycylspermine (DOGS, Polyplus transfection), polyethyleneimine (PEI, Polyplus Transfection) according to manufacturer's instruction, 5 hours prior irradiation. A total dose of 30 Gy was delivered in 4-5 weeks: i) 3×2 Gy/week (about one every two days); ii) 5 Gy/week; iii) 15 Gy/2 weeks. The size of tumor was measured 2-3 times a week. Treatment by irradiation and intratumoral injection of MEM medium (the DRIL dilution buffer), was used as a control of irradiation treatment without DRIL (MEM). The volume of tumor was calculated (V=(a+b²)/2, where a=length, b=width). The ratio of volume measured at t time over the initial volume ($V_t/V_i$) was used as indicator of tumor progression. The mice were followed up to 100 days. At least 4 independent series of six animals were tested.

The results are illustrated by FIG. 4 (Panel A: Untreated arm (n=38); Panel B: control arm with 20 µl culture medium (MEM)+3×2 Gy/week irradiation (n=30); Panel C: the arm with 1 nmole (20 µg) DRIL32-PEG+3×2 Gy/week irradiation (n=35). MEM or DRIL32-PEG was delivered by intratumoral injection 5 hours prior irradiation. The split irradiation dose (2 Gy) was given one of every two days, three times a week. The treatment lasted 5 weeks totalling 30 Gy irradiation. The dots represent the time course of tumor volume of each mouse. The solid lines are the best polynomial fitting. Panel D shows a Kaplan-Meyer plot of all mice of which the increase in tumor volume ($V_t/V_i$)<5).

A significant amount of data has been accumulated on the arm of DRIL32-PEG with 3×2 Gy/week irradiation (panel C, n=35) which clearly showed radiosensitization as compared to the control arms: untreated (panel A, n=38), MEM+3×2 Gy (panel B, n=30). The Man and Whitney statistical test gave p-value=0.00067 for the arm of DRIL32-PEG+3×2 Gy versus MEM+3×2 Gy. The same trend was observed in a Kaplan-Meyer plot of mice with a tumor volume ($V_t/V_i$<5) smaller than five-fold the initial volume (panel D).

Further investigations were subsequently carried out on mice with xenografted human larynx tumors in order to define molecular features of DRIL molecules and optimal protocol for in vivo activity. The data obtained from the studied cohort were consistent with molecular features of DRIL molecules observed in biochemical and in vitro studies (cf. examples 2, 3 and 4). In addition, it was shown that:

1) the fractionation of irradiation, 3×2 Gy per week, gave the best radiosensitization, in reminiscence to the human clinical protocol;
2) the radiosensitization is dose-dependent: 1 nmole (20 µg) DRIL32-PEG>0.3 nmole (6 µg) DRIL32-PEG, no effect at 0.1 nmole (2 µg) DRIL32-PEG;
3) the radiosensitization is dependent on the dwell time between the intratumoral injection of DRIL32-PEG and the ionizing radiation: 5 hours>>1 hour;
4) the DRIL molecules must be used with transfection agents (superfect, DOGS or PEI) according to manufacturer's instruction.

Histological staining of tumor cross section and magnetic resonance imaging revealed the presence of necrosis after the combined treatment of DRIL molecules associated with radiotherapy.

Radio-sensitization was also observed in mice xenografted with human glioblastome tumors. The glioblastome is the highest grade of brain tumor, and is characterized by its extraordinary aggressive progression with fast fatal outcome and resistance to radio- and chemotherapies. 2-3 millions of U87 cells derived from human glioblastome was first injected subcutaneously in nude mouse. The grafted tumor was then took out and used to seed subsequently other nude mice by subcutaneous transplant of about 8 mm³ glioblastome tumor. Table 2 shows data of a pilot series of xenografted human glioblastome tumors on nude mice. 50% mice in the arm which received DRIL32-PEG (1 nmole) by intratumoral injection and irradiation (1×15 Gy/week or 3×5 Gy/week, followed by one week rest, then second treatment cycle, the total dose of ionizing radiation was 30 Gy) had tumor volume<4 cm³ at the day 25 after the start of treatment, whereas 100% mice in the control arms (untreated or irradiated and injected with saline solution (PBS)) had tumor volume well exceeded 4 cm³, and were killed before the end of the assay according to current regulation on animal ethics before the end of the treatment.

TABLE 2

Assay of radiosensitization of xenografted human glioblastome on nude mice by DRIL32-PEG (1 nmole/intratumoral injection). Two protocols of irradiation were used: 1 × 15 Gy/week, or 3 × 5 Gy/week, followed by one week rest, the second irradiation cycle. The total irradiation dose was 30 Gy. Control groups were the untreated or the group received saline solution (PBS) injection.

| Assay groups (xenografted Glioblastome) | Number of mice where Tumor volume <4 cm³ At the day 25 (6 mice per group) |
|---|---|
| Untreated | 0/6 |
| PBS + 1 × 15 Gy/week | 0/6 |
| DRIL32-PEG + 1 × 15 Gy/week | 3/6 |
| PBS + 3 × 5 Gy/week | 0/6 |
| DRIL32-PEG + 3 × 5 Gy/week | 3/6 |

In conclusion, the significant reduction in tumor progression of two human radio-resistant tumors (larynx and glioblastome) xenografted on nude mice provides evidence that the DRIL molecules can efficiently radiosensitize the effect of radiotherapy on these aggressive radio-resistant tumors. Thus, proof of principle of DNA bait approach has been achieved in vivo.

EXAMPLE 6

Chemosensitization of the Treatment of Digestive Tumors Induced in K-Ras$^{V12G}$×Apc$^{1638N}$ Transgenic Mice An endogenous mouse tumor model was chosen to assess the ability of DRIL molecules to sensitize anticancer chemotherapy. To this end, transgenic mice carrying K-Ras$^{V12G}$ and Apc$^{1638N}$ mutations were used. They were obtained by breeding two transgenic mice: one carries K-Ras$^{V12G}$ mutant under the control of the mouse villin promoter (pVill/K-Ras$^{V12G}$) (Janssen et al., 2002), the other contains Apc$^{1638N}$ mutation in one allele (Fodde et al., 1994). Transgenic mice with pVill/K-Ras$^{V12G}$×Apc$^{1638N}$ mutations developed spontaneous tumors in the digestive tract at the age of about 5 months and died rapidly.

They were treated at the mean age of 12 weeks by a combination of chemotherapy (5FU+CPT11) and of DRIL32-PEG versus chemotherapy alone, according to the protocol shown in FIG. 5.1 panel A. The protocol includes three treatment cycles. Each cycle consists of intraperitoneal injection of 0.6 mg 5FU and 0.6 mg CPT11, along with 0.1 mg DRIL32-PEG by oral administration, three times a week, followed by one week rest. 5FU (5 fluorouracile, Teva) was prepared in 0.9% NaCl solution at the concentration of 50 mg/ml. CPT11/Irinotecan (Campto, Aventis) was prepared in 0.9% NaCl solution at the concentration of 20 mg/ml. The health status and survival of the mice were monitored till the death. No clinical indication of additional toxic effect due to DRIL molecules was observed.

The results are given on FIG. 5.1. Panel A: Treatment protocol for three groups/arms of the K-Ras$^{V12G}$×Apc$^{1638N}$ transgenic mice at the mean age of 12 weeks: the control group (untreated), the group treated by 5FU+CPT11, the group treated by 5FU+CPT11 and DRIL32-PEG. It was performed by three cycles of treatment. Each cycle consists of intraperitoneal injection of 0.6 mg 5FU and 0.6 mg CPT11, along with 0.1 mg DRIL32-PEG by oral administration, three times a week, followed by one week rest. The number of mice involved in each groups is indicated in parenthesis. The end point is the time of survival; Panel B: Kaplan-Meyer plot of survival curves of the three groups; Panel C: The median survival time of three groups as shown in panel B.

Despite reduced cohort, a significant improvement of survival time was observed in the arm which received the combination of chemotherapy (5FU+11CPT) and DRIL32-PEG (median survival=226 days, p-value=0.2), as compared to that of chemotherapy alone (173 days) and control arm (175 days) (panel B and C). Additional assays are currently underway to increase the cohort of 5FU+CPT11+DRIL32-PEG and 5FU+CPT11 arms, in order to enhance statistical significance.

A series of mice was sacrificed two weeks after the end of treatment (at the mean age of 18 weeks) in order to evaluate the mean number of tumors per animal. The intestine was examined by macroscopy and histology examination (standard staining by Hematoxyline-Eosine-Safran).

The results are given on FIG. 5.2. The number of animals in each group was indicated in parenthesis. All mice were sacrificed two weeks (week 18) after the protocol shown in FIG. 5.1 panel A. The mean number of the control arm (untreated group, n=101) is 30.8/animal.

Both examinations consistently showed a significant reduction of tumor numbers (>30%) in the arm which received the combination of 5FU+CPT11 and DRIL32-PEG (n=8) as compared to the arm which received chemotherapy alone (n=7) (FIG. 5.2). It is worthy to note that the mean number of the control arm (untreated group, n=101) is 30.8/animal.

Tumor samples prepared from animals treated with DRIL molecules tagged by fluorescein (DRIL32-FITC) and 5FU+CPT11 were analysed using immunofluorescence staining methods. H2AX labelled foci were costained with fluorescent DRIL molecules, in reminiscence of the in vitro finding (cf. example 3.3 and 4). FIG. 6.3 shows an additional assay where a 18 week-old K-Ras$^{V12G}$×Apc$^{1638N}$ transgenic mouse was consecutively treated by chemotherapy (5FU+CPT11) and DRIL32-FITC for three days and sacrificed two hours later after the last treatment as indicated in the panel A. The intestine was taken out and washed by PBS. Then the tumor tissues were sampled and frozen at −80° C. For the analysis, 5 µm histological samples were made from the frozen tumor tissues by cryostat. DNA repair foci were detected by immunofluorescence with polyclonal rabbit anti-γ-H2AX antibody (Trevigen) diluted ⅕₀₀ in PBS, then with goat anti-rabbit antibody tagged by cyanine 3 (Jackson) diluted ½₀₀ in PBS. The samples were also counterstained by DAPI (Sigma). Samples were visualized by epifluorescence microscopy. It was found that the fluorescence of DRIL32-FITC was heterogeneously disseminated in tumor tissues (epithelium and stroma between glandular structures) and had preferential nucleus localization (FIG. 6.3, panel B, left). Similar pattern was found for γ-H2AX sites (FIG. 6.3, panel B, right). The colocalized DRIL32-FITC and γ-H2AX signals were observed almostly.

In conclusion, the improvement of survival and the reduction of tumor number per animal consistently show the evidence of chemosensitization of the treatment of digestive tumors in the transgenic mice carrying K-Ras$^{V12G}$ and Apc$^{1638N}$ mutations by DRIL molecules (DRIL32-PEG). In-depth analysis of tumor tissues in treated animals provides evidence that DRIL molecules interfere with DNA repair process.

It should be pointed out that the oral administration of DRIL32-PEG molecules did not include any transfection agent in this study.

To sum up, biochemical and in vitro data are clearly consistent with a mechanism of action of DRIL molecules through interference with DSB repair by NHEJ pathway, and the repair signal transduction pathway caused by direct or indirect DNA damage (ionizing radiation or chemotherapeutic agents). Due to the nature of NHEJ pathway (sequence-independent pathway), there is no limitation on the sequences and the length of DRIL molecules (Jackson, 2002; Barnes, 2001, Downs & Jackon, 2004). In vivo studies have confirmed efficient radio- and chemo-sensitization of tumors in mice by DRIL molecules. Taken together, all data have consistently provided with proofs of concept of the DNA Bait approach, characterized the molecular features of DRIL molecules.

REFERENCES

Barnes, D. E. Non-homologous end joining as a mechanism of DNA repair. *Curr. Biol.* (2001) 11, R455-7.

Belenkov A I, Paiement J P, Panasci L C, Monia B P, Chow T Y. An antisense oligonucleotide targeted to human Ku80 messenger RNA sensitizes M059K malignant glioma cells to ionizing radiation, bleomycin, and etoposide but not DNA cross-linking agents. Cancer Res. (2002), 62, 5888-96.

Boulton, S.; Kyle, S.; Durkacz, B. W. Mechanisms of enhancement of cytotoxicity in etoposide and ionising radiation-treated cells by the protein kinase inhibitor wortmannin. *Eur. J. Cancer* (2000), 36, 535-41.

Cantor, C. R.; Warshaw, M. M.; Shapiro, H. Oligonucleotide interactions. III. Conformational differences between deoxy- and ribodinucleoside phosphates *Biopolymers* (1970), 9, 1059-77.

Cary, R. B.; Peterson, S. R.; Wang, J. T.; Bear, D. G.; Bradbury, E. M. & Chen, D. J. DNA looping by Ku and the DNA-dependent protein kinase. *Proc. Natl. Acad. Sci. USA* (1997) 94, 4267-4272.

Downs, J. A.; Jackson, S. P A means to a DNA end: The many roles of Ku. *Nat. Rev. Mol. Cell. Biol.* (2004), 5, 367-78.

Durant, S.; Karran, P. Vanillins—a novel family of DNA-PK inhibitors. *Nucleic Acids Res.* (2003), 31, 5501-12.

Fodde, R.; Edelmann, W.; Yang, K.; van Leeuwen, C.; Carlson, C.; Renault, B.; Breukel, C.; Alt, E.; Lipkin, M.; Khan, P. M. A targeted chain-termination mutation in the mouse Apc gene results in multiple intestinal tumors. *Proc Natl Acad Sci USA*. (1994), 91, 8969-73.

Jackson, S. P. Sensing and repairing DNA double-strand breaks. *Carcinogenesis*. (2002), 23, 687-96.

Janssen, K. P.; el-Marjou, F.; Pinto, D.; Sastre, X.; Rouillard, D.; Fouquet, C.; Soussi, T.; Louvard, D.; Robine, S. Targeted expression of oncogenic K-ras in intestinal epithelium causes spontaneous tumorigenesis in mice. *Gastroenterology* (2002), 123, 492-504.

Kim, C. H.; Park, S. J.; Lee, S. H.; A targeted inhibition of DNA-dependent protein kinase sensitizes breast cancer cells following ionizing radiation. *J. Pharmacol. Exp. Ther.* (2002), 303, 753-9.

Lee, H.; Sun, D.; Larner, J. M.; Wu, F. S. The tumor suppressor p53 can reduce stable transfection in the presence of irradiation. *J. Biomed Sci.* (1999), 6, 285-92.

Li, S.; Takeda, Y.; Wragg, S.; Barrett, J.; Phillips, A.; Dynan, W. S. Modification of the ionizing radiation response in living cells by an scFv against the DNA-dependent protein kinase. *Nucleic Acid Res.* (2003) 31, 5848-57.

Li, G. C.; He, F.; Shao, X.; Urano, M.; Shen, L.; Kim, D.; Borrelli, M.; Leibel, S. A.; Gutin, P. H.; Ling, C. C. Adenovirus-mediated heat-activated antisense Ku70 expression radiosensitizes tumor cells in vitro and in vivo. *Cancer Res.* (2003b), 63, 3268-74.

Maacke, H.; Jost, K.; Opitz, S.; Miska, S.; Yuan, Y.; Hasselbach, L.; Luttges, J.; Kalthoff, H.; Sturzbecher, H. W. DNA repair and recombination factor Rad51 is over-expressed in human pancreatic adenocarcinoma. *Oncogene* (2000). 19, 2791-5.

Mallya, S. M.; Sikpi, M. O. Evidence of the involvement of p53 in gamma-radiation-induced DNA repair in human lymphoblasts. *Int. J. Radiat. Biol.* (1998), 74, 231-8.

Marangoni, E.; Bay, J. O.; Verrelle, P.; Bourhis, J. Tranfert de gène pour modifier la réponse à la radithérapie? *Cancer Radiother.* (2000), 4, 175-80.

Marangoni, E.; Le Romancer, M.; Foray, N.; Muller, C.; Douc-Rasy, S.; Vaganay, S.; Abdulkarim, B.; Barrois, M.; Calsou, P.; Bernier, J.; Salles, B.; Bourhis, J. Transfer of Ku80 RNA antisense decreases the radioresistance of human fibroblasts. *Cancer Gene Ther.* (2000b), 7, 339-46.

Marangoni, E.; Foray, N.; O'Driscoll, M.; Douc-Rasy, S.; Bernier, J.; Bourhis, J.; Jeggo, P. A Ku80 fragment with dominant negative activity imparts a radiosensitive phenotype to CHO-K1 cells. *Nucleic Acid Res.* (2000a), 28, 4778-82.

Marangoni, E.; Le Romancer, M.; Foray, N.; Muller, C.; Douc-Rasy, S.; Vaganay, S.; Abdulkarim, B.; Barrois, M.; Calsou, P.; Bernier, J.; Salles, B.; Bourhis J. Transfer of Ku80 RNA antisense decreases the radioresistance of human fibroblasts. *Cancer Gene Ther.* (2000b), 7, 339-46.

Martensson, S.; Hammarsten, O. DNA-dependent protein kinase catalytic subunit: structural requirements for kinase activity by DNA ends. *J. Biol. Chem.* (2002), 277, 3020-29.

Mimori, T.; Hardin, J. A. Mechanism of interaction between Ku protein and DNA. *J. Biol. Chem.* (1986), 261, 10375-10379.

Nimura, Y.; Ismail, S. M.; Kurimas, A.; Chen, D. J.; Stevens, C. W. DNA-PK and ATM are required for radiation-enhanced integration. *Radiat Res.* (2002), 157, 562-7.

O'Driscoll, M.; Jeggo, P. Immunological disorders and DNA repair. *Mutat Res.* (2002), 509, 109-26.

Ohnishi, T.; Taki, T.; Hiraga, S.; Arita, N.; Morita, T. In vitro and in vivo potentiation of radiosensitivity of malignant gliomas by antisense inhibition of the RAD51 gene. *Biochem Biophys Res Commun.* (1998), 245, 319-24.

Pang, D. L.; Yoo, S. H.; Dynan, W. S.; Jung, M.; Dritschilo, A. Ku proteins join DNA fragments as shown by atomic force microscopy. *Cancer Res.* (1997), 57, 1412-5.

Peng, Y.; zhang, Q.; Nagasawa, H.; Okayasu, R.; Liber, H. L.; Bedford, J. S. Silencing expression of the catalytic subunit of DNA-dependent protein kinase by small interfering RNA sensitizes human cells for radiation-induced chromosome damage, cell killing, and mutation. *Cancer Res.* (2002), 62, 6400-4.

Rassool, F. V. DNA double strand breaks (DSB) and non-homologous end joining (NHEJ) pathways in human leukemia. *Cancer Lett.* (2003), 193, 1-9.

Roddam, P. L.; Rollinson, S.; O'Driscoll, M.; Jeggo, P. A.; Jack, A.; Morgan, G. J. Genetic variants of NHEJ DNA ligase IV can affect the risk of developing multiple myeloma, a tumour characterised by aberrant class switch recombination. *J. Med. Genet.* (2002) 39, 900-5.

Sak, A.; Stuschke, M.; Wurm, R.; Schroeder, G.; Sinn, B.; Wolf, G.; Budach, V. Selective inactivation of DNA-dependent protein kinase with antisense oligodeoxynucleotides: consequences for the rejoining of radiation-induced DNA double-strand breaks and radiosensitivity of human cancer cell lines. *Cancer Res.* (2002), 62, 6621-24.

Stevens, C. W.; Zeng, M.; Cerniglia, G. J. Ionizing radiation greatly improves gene transfer efficiency in mammalian cells. *Hum Gene Ther.* (1996), 7, 1727-34.

Stevens, C. W.; Stamato, T. D., Mauldin, S. K.; Getts, R. C.; Zeng, M.; Cerniglia, G. J. Radiation-induced recombination is dependent on KU80. *Radiat Res.* (1999), 151, 408-13.

Stevens, C. W.; Cerniglia, G. J.; Giandomenico, A. R.; Koch, C. J. DNA damaging agents improve stable gene transfer efficiency in mammalian cells. *Radiat Oncol Investig.* (1998), 6, 1-9.

Verrelle, P.; Bourhis, J. Modulation de la réponse cellulaire aux radiations ionisantes: vers de nouvelles cibles moléculaires? *Cancer Radiother.* (1997), 1, 484-93.

Walker, J. R.; Corpina, R. A.; Goldberg, J. Structure of the Ku heterodimer bound to DNA and its implications for double-strand break repair. *Nature* (2001), 412, 607-14.

Yoo, S. H.; Dynan, W. S. Characterization of the RNA binding properties of Ku protein. *Biochemsitry* (1998), 37, 1336-43.

Yoo, S. H.; Kimzey, A.; Dynan, W. S. Photocross-linking of an oriented DNA repair complex. Ku bound at a single DNA end *J. Biol. Chem.* (1999), 274, 20034-9.

Yoo, S. H.; Dynan, W. S. Geometry of a complex formed by double strand break repair proteins at a single DNA end: recruitment of DNA-PKcs induces inward translocation of Ku protein. *Nucleic Acid Res.* (1999), 27, 4679-86.

Zhao, J. K.; Wang, J. T.; Chen, D. J.; Peterson, S. R.; Trewhella, J. The solution structure of the DNA double-stranded break repair protein Ku and its complex with DNA: a neutron contrast variation study. *Biochemistry* (1999), 38, 2152-9.

The invention claimed is:

1. A method of enhancing tumor sensitivity to DNA damaging anticancer therapy, the method comprising administering to a subject a nucleic acid molecule, wherein said molecule comprises a double stranded portion of at least 24 bp, has at least one free end, and wherein said molecule is substrate for binding by at least a Ku protein involved in the NHEJ pathway of double strand breaks repair.

2. A method of treating cancer, the method comprising administering to a subject a nucleic acid molecule, wherein said molecule comprises a double stranded portion of at least 24 bp, has at least one free end, and wherein said molecule is substrate for binding by at least a Ku protein involved in the NHEJ pathway of double strand breaks repair, in combination with a DNA damaging anticancer therapy.

3. The method of claim 2, wherein the DNA damaging anticancer therapy is selected from radiotherapy and chemotherapy.

4. The method of claim 3, wherein the molecule is administered prior to radiotherapy.

5. The method of claim 3, wherein the molecule is administered prior to or along with chemotherapy.

6. The method of claim 1, wherein the cancer is selected from glioblastoma, breast cancer and cervical cancer.

7. The method of claim 1, wherein the molecule is administered by intravenous, intra-tumoral or sub-cutaneous injection, or by oral route.

8. The method of claim 1 or claim 2, wherein said molecule comprises between 24 and 100 bp.

9. The method of claim 1 or claim 2, wherein said molecule is a linear or a hairpin nucleic acid molecule.

10. The method of claim 9, wherein said molecule is a hairpin nucleic acid molecule and wherein the loop comprises nucleic acid or chemical groups.

11. The method of claim 1 or claim 2, wherein at least one free end of said molecule is blunt or 5'- or 3'-protruding.

12. The method of claim 1 or claim 2, wherein said molecule is capable of being up-taken by cell into the cell nucleus.

13. The method of claim 1 or claim 2, wherein said molecule comprises a phosphodiester backbone or a chemically modified phosphodiester backbone, or another backbone with one or several chemical groups.

14. The method of claim 1 or claim 2, wherein said molecule comprises a 2'-deoxynucleotide backbone, and optionally comprises one or several 2'-ribonucleotides or other modified nucleotides or nucleobases other than adenine, cytosine, guanine and thymine.

15. The method of claim 13, wherein said backbone comprises methylphosphonates, phosphoramidates, morpholino nucleic acid, 2'-O,4'-C methylene/ethylene bridged locked nucleic acid, peptide nucleic acid (PNA), short chain alkyl, or cycloalkyl intersugar linkages or short chain heteroatomic or heterocyclic intrasugar linkages of variable length.

16. The method of claim 1 or claim 2, wherein said molecule comprises one or several chemical groups at the end of each strand or, at least, at the 3' end of each strand.

17. The method of claim 16, wherein said molecule comprises one or several phosphorothioates at the end of each strand or, at least, at the 3'end of each strand.

18. The method of claim 1 or claim 2, wherein said molecule further comprises at least one embedded element, which hampers DNA replication or DNA repair, said at least one element being incorporated in the centre or at the end of the double-stranded molecule.

19. The method of claim 10, wherein said loom comprises
a) a polyethyleneglycol chain or any hydrocarbon chain, optionally interrupted and/or substituted by one or more heteroatoms or heteroatomic or heterocyclic groups, comprising one or several heteroatoms; or
b) a native oligonucleotide.

20. The method of claim 1 or claim 2, wherein said molecule is made by chemical synthesis, semi-biosynthesis or biosynthesis.

21. The method of claim 19, wherein said native oligonucleotide is a tetradeoxythymidylate.

22. The method of claim 1 or claim 2, wherein said molecule is 32 bp.

* * * * *